United States Patent
Li et al.

(10) Patent No.: US 8,876,691 B2
(45) Date of Patent: *Nov. 4, 2014

(54) SURGICAL SLINGS

(71) Applicant: Boston Scientific Scimed, Inc., Maple Grove, MN (US)

(72) Inventors: Jianmin Li, Lexington, MA (US); Michael Madden, Princeton, MA (US); Hamid Davoudi, Westwood, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/036,856

(22) Filed: Sep. 25, 2013

(65) Prior Publication Data

US 2014/0031610 A1  Jan. 30, 2014

Related U.S. Application Data

(63) Continuation of application No. 11/360,460, filed on Feb. 23, 2006, now Pat. No. 8,545,386, which is a continuation-in-part of application No. 10/918,123, filed on Aug. 13, 2004, now Pat. No. 8,337,386.

(60) Provisional application No. 60/495,439, filed on Aug. 14, 2003.

(51) Int. Cl.
*A61F 2/02* (2006.01)
*A61F 2/00* (2006.01)

(52) U.S. Cl.
CPC ....... *A61F 2/0045* (2013.01); *A61F 2210/0004* (2013.01); *A61F 2250/0031* (2013.01); *A61F 2250/0051* (2013.01)

USPC ............................................................ 600/30

(58) Field of Classification Search
USPC ......... 600/29–30, 37; 128/885; 606/151, 157; 623/23.64–23.67; 424/426

See application file for complete search history.

(56) References Cited

U.S. PATENT DOCUMENTS

| | | |
|---|---|---|
| 3,565,073 A | 2/1971 | Giesy |
| 3,704,712 A | 12/1972 | Giesy et al. |
| 3,789,828 A | 2/1974 | Schulte |
| 4,798,193 A | 1/1989 | Giesy et al. |
| 4,824,435 A | 4/1989 | Giesy et al. |
| 4,872,451 A | 10/1989 | Moore et al. |
| 4,946,467 A | 8/1990 | Ohi et al. |
| 4,946,468 A | 8/1990 | Li |

(Continued)

FOREIGN PATENT DOCUMENTS

| | | |
|---|---|---|
| EP | 0677297 | 12/2000 |
| SU | 1225547 A1 | 4/1986 |

(Continued)

OTHER PUBLICATIONS

Fred E. Govier, et al., "Pubovaginal Slings: A Review of the Technical Variables," Current Opinion in Urology, 11: pp. 405-410, 2001.

(Continued)

*Primary Examiner* — Christine Matthews

(57) ABSTRACT

The invention relates generally to surgical implants, and in various embodiments to surgical implants configured for promoting growth of collagenous tissue at an anatomical site.

20 Claims, 7 Drawing Sheets

(56) References Cited

U.S. PATENT DOCUMENTS

| | | |
|---|---|---|
| 5,002,550 A | 3/1991 | Li |
| 5,037,429 A | 8/1991 | Hermes et al. |
| 5,064,435 A | 11/1991 | Porter |
| 5,078,730 A | 1/1992 | Li et al. |
| 5,084,058 A | 1/1992 | Li |
| 5,087,263 A | 2/1992 | Li |
| 5,112,344 A | 5/1992 | Petros |
| 5,152,749 A | 10/1992 | Giesy et al. |
| 5,207,679 A | 5/1993 | Li |
| 5,250,033 A | 10/1993 | Evans et al. |
| 5,256,150 A | 10/1993 | Quiachon et al. |
| 5,334,185 A | 8/1994 | Giesy et al. |
| 5,342,557 A * | 8/1994 | Kennedy ............ 264/8 |
| 5,368,595 A | 11/1994 | Lewis |
| 5,383,904 A | 1/1995 | Totakura et al. |
| 5,395,349 A | 3/1995 | Quiachon et al. |
| 5,439,467 A | 8/1995 | Benderev et al. |
| 5,456,722 A | 10/1995 | McLeod et al. |
| 5,505,735 A | 4/1996 | Li |
| 5,540,703 A | 7/1996 | Barker, Jr. et al. |
| 5,611,515 A | 3/1997 | Benderev et al. |
| 5,645,589 A | 7/1997 | Li |
| 5,674,285 A | 10/1997 | Quaid |
| 5,683,418 A | 11/1997 | Luscombe et al. |
| 5,690,649 A | 11/1997 | Li |
| 5,702,215 A | 12/1997 | Li |
| 5,742,943 A | 4/1998 | Chen |
| 5,749,884 A | 5/1998 | Benderev et al. |
| 5,840,011 A | 11/1998 | Landgrebe et al. |
| 5,853,745 A | 12/1998 | Darouiche |
| 5,860,993 A | 1/1999 | Thompson et al. |
| 5,899,906 A | 5/1999 | Schenk |
| 5,899,909 A | 5/1999 | Claren et al. |
| 5,934,283 A | 8/1999 | Willem et al. |
| 5,935,122 A | 8/1999 | Fourkas et al. |
| 5,954,057 A | 9/1999 | Li |
| 6,039,686 A | 3/2000 | Kovac |
| 6,042,534 A | 3/2000 | Gellman et al. |
| 6,042,536 A | 3/2000 | Tihon et al. |
| 6,042,592 A | 3/2000 | Schmitt |
| 6,050,937 A | 4/2000 | Benderev |
| 6,053,935 A | 4/2000 | Brenneman et al. |
| 6,096,041 A | 8/2000 | Gellman et al. |
| 6,099,547 A | 8/2000 | Gellman et al. |
| 6,110,101 A | 8/2000 | Tihon et al. |
| 6,147,135 A | 11/2000 | Yuan et al. |
| 6,156,572 A | 12/2000 | Bellamkonda et al. |
| 6,162,962 A | 12/2000 | Hinsch et al. |
| 6,197,036 B1 | 3/2001 | Tripp et al. |
| 6,200,330 B1 | 3/2001 | Benderev et al. |
| 6,264,676 B1 | 7/2001 | Gellman et al. |
| 6,273,852 B1 | 8/2001 | Lehe et al. |
| 6,306,079 B1 | 10/2001 | Trabucco |
| 6,319,264 B1 * | 11/2001 | Tormala et al. ............ 606/151 |
| 6,375,662 B1 | 4/2002 | Schmitt |
| 6,382,214 B1 | 5/2002 | Raz et al. |
| 6,387,041 B1 | 5/2002 | Harari et al. |
| 6,406,423 B1 | 6/2002 | Scetbon |
| 6,423,080 B1 | 7/2002 | Gellman et al. |
| D466,213 S | 11/2002 | Snitkin et al. |
| 6,478,727 B2 | 11/2002 | Scetbon |
| 6,482,645 B2 | 11/2002 | Atala |
| 6,491,703 B1 | 12/2002 | Ulmsten |
| 6,494,887 B1 | 12/2002 | Kaladelfos |
| 6,530,943 B1 | 3/2003 | Hoepffner et al. |
| 6,548,569 B1 | 4/2003 | Williams et al. |
| 6,582,443 B2 | 6/2003 | Cabak et al. |
| 6,596,001 B2 | 7/2003 | Stormby et al. |
| 6,596,002 B2 | 7/2003 | Therin et al. |
| 6,599,235 B2 | 7/2003 | Kovac |
| 6,599,524 B2 | 7/2003 | Li et al. |
| 6,605,097 B1 | 8/2003 | Lehe et al. |
| 6,612,977 B2 | 9/2003 | Staskin et al. |
| 6,638,209 B2 | 10/2003 | Landgrebe |
| 6,638,210 B2 | 10/2003 | Berger |
| 6,638,211 B2 | 10/2003 | Suslian et al. |
| 6,641,524 B2 | 11/2003 | Kovac |
| 6,641,525 B2 | 11/2003 | Rocheleau et al. |
| 6,648,921 B2 | 11/2003 | Anderson et al. |
| 6,652,450 B2 | 11/2003 | Neisz et al. |
| 6,660,301 B1 | 12/2003 | Vogel et al. |
| 6,666,817 B2 | 12/2003 | Li |
| 6,669,706 B2 | 12/2003 | Schmitt et al. |
| 6,685,629 B2 | 2/2004 | Therin |
| 6,689,047 B2 | 2/2004 | Gellman |
| 6,755,781 B2 | 6/2004 | Gellman |
| 6,802,807 B2 | 10/2004 | Anderson et al. |
| 6,830,052 B2 | 12/2004 | Carter et al. |
| 6,881,184 B2 | 4/2005 | Zappala |
| 6,953,428 B2 | 10/2005 | Gellman et al. |
| 7,083,568 B2 | 8/2006 | Neisz et al. |
| 7,087,065 B2 | 8/2006 | Ulmsten et al. |
| 7,198,597 B2 | 4/2007 | Siegel et al. |
| 7,267,645 B2 | 9/2007 | Anderson et al. |
| 8,337,386 B2 | 12/2012 | Li et al. |
| 2002/0022841 A1 | 2/2002 | Kovac |
| 2002/0055748 A1 | 5/2002 | Gellman et al. |
| 2002/0072694 A1 | 6/2002 | Snitkin et al. |
| 2002/0077526 A1 | 6/2002 | Kammerer et al. |
| 2002/0083820 A1 * | 7/2002 | Greenhalgh ............ 87/8 |
| 2002/0090725 A1 | 7/2002 | Simpson et al. |
| 2002/0091373 A1 | 7/2002 | Berger |
| 2002/0095181 A1 | 7/2002 | Beyar |
| 2002/0103542 A1 | 8/2002 | Bilbo |
| 2002/0107429 A1 | 8/2002 | Wironen |
| 2002/0116025 A1 | 8/2002 | Haab |
| 2002/0119179 A1 | 8/2002 | Rezania et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151909 A1 | 10/2002 | Gellman et al. |
| 2002/0151910 A1 | 10/2002 | Gellman et al. |
| 2002/0151968 A1 | 10/2002 | Zilla et al. |
| 2002/0156487 A1 | 10/2002 | Gellman et al. |
| 2002/0156488 A1 | 10/2002 | Gellman et al. |
| 2002/0156489 A1 | 10/2002 | Gellman et al. |
| 2002/0161382 A1 | 10/2002 | Neisz et al. |
| 2002/0183588 A1 | 12/2002 | Fierro |
| 2003/0004580 A1 | 1/2003 | Sump et al. |
| 2003/0009181 A1 | 1/2003 | Gellman et al. |
| 2003/0010929 A1 | 1/2003 | Priewe et al. |
| 2003/0023135 A1 | 1/2003 | Ulmsten et al. |
| 2003/0028075 A1 | 2/2003 | Ulmsten et al. |
| 2003/0065246 A1 | 4/2003 | Inman et al. |
| 2003/0087111 A1 | 5/2003 | Hubbell et al. |
| 2003/0100954 A1 | 5/2003 | Schuldt-Hempe et al. |
| 2003/0130670 A1 | 7/2003 | Anderson et al. |
| 2003/0158607 A1 | 8/2003 | Carr et al. |
| 2003/0171644 A1 | 9/2003 | Anderson et al. |
| 2003/0176762 A1 | 9/2003 | Kammerer |
| 2003/0195386 A1 | 10/2003 | Thierfelder et al. |
| 2004/0006353 A1 | 1/2004 | Bosley et al. |
| 2004/0073234 A1 | 4/2004 | Chu et al. |
| 2004/0087970 A1 | 5/2004 | Chu et al. |
| 2004/0116944 A1 | 6/2004 | Chu et al. |
| 2004/0225181 A1 | 11/2004 | Chu et al. |
| 2004/0230206 A1 | 11/2004 | Gellman et al. |
| 2004/0249240 A1 | 12/2004 | Goldmann et al. |
| 2005/0010748 A1 | 1/2005 | Osborn |
| 2005/0027220 A1 | 2/2005 | Wagner et al. |
| 2005/0038451 A1 | 2/2005 | Rao et al. |
| 2005/0038452 A1 | 2/2005 | Chu |
| 2005/0043820 A1 | 2/2005 | Browning |
| 2005/0075660 A1 | 4/2005 | Chu et al. |
| 2005/0096499 A1 | 5/2005 | Li et al. |
| 2005/0131392 A1 | 6/2005 | Chu et al. |
| 2005/0131393 A1 | 6/2005 | Chu et al. |
| 2006/0205998 A1 | 9/2006 | Li et al. |

FOREIGN PATENT DOCUMENTS

| | | |
|---|---|---|
| SU | 1443873 A1 | 12/1988 |
| WO | 9606567 A1 | 3/1996 |
| WO | 9713465 A1 | 4/1997 |

(56) References Cited

FOREIGN PATENT DOCUMENTS

| | | |
|---|---|---|
| WO | 9834545 A1 | 8/1998 |
| WO | 9835632 A1 | 8/1998 |
| WO | 0074594 A1 | 12/2000 |
| WO | 0074633 A1 | 12/2000 |
| WO | 0145588 A1 | 6/2001 |
| WO | 0219945 A2 | 3/2002 |
| WO | 0222184 A2 | 3/2002 |
| WO | 0230293 A1 | 4/2002 |
| WO | 0240242 A1 | 5/2002 |
| WO | 02058563 A1 | 8/2002 |
| WO | 02078571 A1 | 10/2002 |
| WO | 03007847 A1 | 1/2003 |
| WO | 03013392 A1 | 2/2003 |
| WO | 2005007019 A2 | 1/2005 |
| WO | 2005016184 A1 | 2/2005 |

OTHER PUBLICATIONS

John Klutke, et al., "The Promise of Tension-Free Vaginal Tape for Female SUI," Contemporary Urology, Oct. 2000, pp. 59-73.

B. G. Volkmer, et al., "Surgical Intervention for Complications of the Tension-Free Vaginal Tape Procedure", The Journal of Urology, vol. 169, Feb. 2003, pp. 570-574.

M. Tirrell, et al., "The Role of Surface Science in Bioengineered Materials" Surface Science, 500 (2002) pp. 61-83.

M. Spector, "Joints: Regeneration of Bone, Cartilage, Meniscus, Ligament, and Tendon", downloaded Jan. 16, 2006 from httQ://ocw.mit.edu/, 20 pages.

A.S.G. Curtis, et al., "An In Vivo Microfabricated Scaffold for Tendon Repair," European Cells and Materials, vol. 9. 2005, pp. 50-57.

J. E. Sanders, et al., "Relative Influence of Polymer Fiber Diameter and Surface Charge on Fibrous Capsule Thickness and Vessel Density for Single-Fiber Implants," Biomed Mater Res A., Jun. 15, 2003; 65(4): pp. 462-467.

J. E. Sanders, et al., "Small Fiber Diameter Fibro-Porous Meshes: Tissue Response Sensitivity to Fiber Spacing," J Biomed Mater Res A. Mar. 1, 2005 ;72(3): pp. 335-342.

J.E. Sanders, et al., "Tissue Response to Single-Polymer Fibers of Varying Diameters: Evaluation of Fibrous Encapsulation and Macrophage Density," J Biome. Mater. Res., Oct. 2000; 52(1), pp. 231-237.

J.E. Sanders, et al., Tissue Response to Microfibers of Different Polymers: Polyester, Polyethylene, Polylactic Acid, and Polyurethane, J Biomed Mater Res. Nov. 2002; 62(2), pp. 222-227.

J.E. Sanders, et al., "Tissue Response to Single Polymer Fibers of Varying Diameters: Results From an In Vivo Model," 1999 Bioengineering Conference Jun. 16-20, 1999, Big Sky, Montana.

J.E. Sanders, et al., "Polymer Microfiber Mechanical Properties: a System for Assessment and Investigation of the Link with Fibrous Capsule Formation," J Biomed Mater Res A., Dec. 15, 2003; 67(4): pp. 1412-1416.

X. T. Wang, et al., "Tendon Healing In Vitro: bFGF Gene Transfer to Tenocytes by Adeno-Associated Viral Vectors Promotes Expression of Collagen Genes," The Journal of Hand Surgery, Nov. 2005; 30(6): pp. 1255-1261.

P. Burssens, et al., "Exogenously Administered Substance P and Neutral Endopeptidase Inhibitors Stimulate Fibroblast Proliferation, Angiogenesis and Collagen Organization During Achilles Tendon Healing," Foot Ankle Inernational, Oct. 2005; 26(10): 832-838.

S. Thomopoulos, et al., "Effect of Several Growth Factors on Canine Flexor Tendon Fibroblast Proliferation and Collagen Synthesis In Vitro," The Journal of Hand Surgery [Am], May 2005; 30(3), pp. 441-447.

T. Tsubone, et al., "Expression of Growth Factors in Canine Flexor Tendon After Laceration in Vivo," Annals of Plastic Surgery, Oct. 2004; 53(4), pp. 393-397.

Notice of Allowance for U.S. Appl. No. 11/360,460, mailed Jun. 3, 2013, 21 pages.

Advisory Action for U.S. Appl. No. 13/724,579, mailed Nov. 26, 2013, 3 pages.

Final Office Action for U.S. Appl. No. 13/724,579, mailed Sep. 13, 2013, 8 pages.

Notice of Allowance for U.S. Appl. No. 13/724,579, mailed Dec. 26, 2013, 9 pages.

Non-Final Office Action Response for U.S. Appl. No. 11/360,460, filed May 13, 2013, 11 pages.

Final Office Action Response for U.S. Appl. No. 13/724,579, filed Nov. 12, 2013, 9 pages.

Non-Final Office Action Response for U.S. Appl. No. 13/724,579, filed Jun. 12, 2013, 17 pages.

Bayer, et al, "A new approach to primary strengthening of colostomy with Marlex mesh to prevent paracolostomy hernia", Surg Gynecol Obstet, vol. 163, No. 6, pp. 579-580, Dec. 1986.

Delorme, "The transobdurator band: a minimmaly invasive procedure for treatment of urinary stress incontinence in women", Progress in Urology, vol. 11, pp. 1306-1313, 2001.

Fianu, et al, "Absorbable Polyglactin Mesh for Retropubic Sling Operation in Female Urinary Stress Incontinence", Gynecol. Obstet. Invest., vol. 16, 1983, pp. 45-50.

Giesy, et al, "Ureteral Instrumentation: A New System for Continued Access Via a Safety Guidewire", Journal of Urology, No. 4, Part 2, p. 282A, 1988.

Gittes, et al, "No-Incision Pubovaginal Suspension for Stress Incontinence", Journal of Urology, vol. 138, No. 3, pp. 568-570, Sep. 1987.

Haab, et al, "Feasibility of Outpatient Percutaneous Bladder Neck Suspension Under Local Anesthesia", Urology vol. 50 No. 4, pp. 585-587, Oct. 1997.

Hakim, et al, "Use of Biodegradable Mesh as a Transport for a Cultured Uroepithelial Graft: An Improved Method Using Collagen Gel", Urology, vol. 44, No. 1, pp. 139-142, 1994.

Jacquelin, "Utilisation du TVT dans la chirurgie de l'incontinence urinaire feminine", J. Gynecol. Obstet Biol Reprod. 29, 242-47, 2000.

Katz, "Developments in Medical Polymers for Biomaterials Applications", Medical Device & Diagnostic Industry Magazine MDDI Article Index, Jan. 2001, http://www.devicelink.com/mddi/archive/01/01/003.html.

Kersey, "The Gauze Hammock Sling Operation in the Treatment of Stress Incontinence", British Journal of Obstetrics and Gynaecology, vol. 90, pp. 945-949, Oct. 1983.

Kovac, et al, "Pubic Bone Suburethral Stabilization Sling for Recurrent Urinary Incontinence", Obstetrics & Gynecology, vol. 89, No. 4, Apr. 1997, pp. 624-627, retrieved from http://journals.lww.com/greenjournal/Abstract/1997/04000/Pubic__Bone.

Matapurkar, et al, "A New Technique of "Marlex-Peritoneal Sandwich" in the Repair of Large Incisional Herias", World Journal of Surgery, vol. 15, No. 6, 768-770, 1991.

Middleton, et al, "Synthetic Biodegradable Polymers as Medical Devices, Medical Plastics and Biomaterials Magazine", MPB Article Index, Mar. 1998, http://www.devicelink.com/mpb/archive/98/03/002.html.

Norris, et al, "Use of Synthetic Material in Sling Surgery: A Minimally Invasive Approach", Journal of Endourology, vol. 10, Issue 3, pp. 227-230, Jun. 1996.

Olsen, et al, "Urethral Reconstruction with a New Synthetic Absorbable Device: An Experimental Study", Scand J. Urol Nephrol 26, pp. 323-326, 1992.

Petros, "Ambulatory Surgery for Urinary Incontinence and Vaginal Prolapse", Medical Journal of Australia, vol. 161, pp. 171-172, 1994.

Petros, et al, "An Integral Theory and Its Method for the Diagnosis and Management of Female Urinary Incontinence", Scandinavian Journal of Urology and Nephrology. Supplement vol. 153, pp. 1-93, 1993.

Petros, et al, "Urethral Pressure Increase on Effort Originates from Within the Urethra, and Continence From Musculovaginal Closure", Neurourology and Urodynamics, vol. 14, No. 4, pp. 337-346, 1995.

Petros, "An Integral Theory of Bladder Neck Opening, Closure and Urinary incontinence in the Female", International Journal of Gynecology & Obstetrics. XXIII World Congress of Gynaecology and Obstetrics (FIGO), 1991.

Petros, "The Intravaginal Slingpasty Operation, a Minimally Invasive Technique for Cure of Urinary Incontinence in the Female", Aust. NZ J Obstet Gynaecol, vol. 36, No. 4, pp. 453-461, 1996.

(56) References Cited

OTHER PUBLICATIONS

Petros, "Medium-term Follow-up of the Intravaginal Slingplasty Operation Indicates Minimal Deterioration of Urinary Continence with Time", Aust NZ J Obstet Gynaecol, vol. 39, No. 3, pp. 354-356, Aug. 1999.
Raz, et al, "Vaginal Wall Sling", The Journal of Urology, vol. 141, pp. 43-46, 1989.
Raz, "Modified Bladder Neck Suspension for Female Stress Incontinence", Urology, vol. 17, No. 1, pp. 82-85, Jan. 1981.
Raz, et al, "Fascial Sling to Correct Male Neurogenic Sphincter Incompetence: The McGuire/Raz Approach", Journal of Urology, vol. 139, No. 3, pp. 528-531, Mar. 1988.
Starney, "Endoscopic Suspension of the Vesical Neck", Stanton, Tanagho (eds.), Surgery of Female Incontinence, Springer-Verlag, Berlin, pp. 115-132, 1986.
Starney, "Endoscopic Suspension of the Vesical Neck for Urinary Incontinence in Females", Annals of Surgery, vol. 192, pp. 465-471, 1980.
Starney, "Endoscopic Suspension of the Vesical Neck for Urinary Incontinence. Surgery", Gynecology & Obstetrics, vol. 136, No. 4, pp. 547-554, 1973.
Staskin, "Sling Surgery for the Treatment of Female", Stress Incontinence, vol. 5 No. 1, pp. 106-122, 1991.
Staskin, et al, "The Gore-tex sling procedure for female sphincteric incontinence: indications, technique, and results", World J of Urol., vol. 15, No. 5, pp. 295-299, 1997.
Sussman, et al, "The Raz Bladder Neck Suspension: Five-Year Experience", The Journal of Urology, vol. 145, p. 223A, 1993.
Ulmsten, et al, "A Multicenter Study of Tension-Free Vaginal Tape (TVT) for Surgical Treatment of Stress Urinary Incontinence", Int Urogynecol J., vol. 9, No. 4, pp. 210-213, 1998.
Ulmsten, et al, "A Three-Year Follow Up of Tension Free Vaginal Tape for Surgical Treatment of Female Stress Urinary Incontinence", British Journal of Obstetrics and Gynaecology, vol. 106, pp. 345-350, 1999.
Ulmsten, et al, "Intravaginal slingplasty", Zentralbl Gynakol, vol. 116, pp. 398-404, 1994.
Ulmsten, et al, "Surgery for female urinary incontinence", Current Opinion in Obstetrics & Gynecology, vol. 4 No. 3, pp. 456-462, 1992.
Ulmsten, "An Introduction to Tension-Free Vaginal Tape (TVT)—A New Surgical Procedure for Treatment of Female Urinary Incontinence", Int Urogynecol J. Pelvic Floor Dysfunct. (Suppl 2), pp. S3-S4, 2001.
Ulmsten, "Connective Tissue Factors in the Aetiology of Female Pelvic Disorders", Ann. Med, vol. 22, No. 6, pp. 403, Dec. 1990.
Ulmsten, "The basic understanding and clinical results of tension-free vaginal tape for stress urinary incontinence", Urology A, pp. 269-273, Jul. 2001.
Ulmsten, et al, "An Ambulatory Surgical Procedure Under Local Anesthesia for Treatment of Female Urinary Incontinence", International Urogynecology Journal, vol. 7, No. 2, pp. 81-86, 1996.
Ulmsten, et al, "Intravaginal Slingplasty (IVS): An Ambulatory Surgical Procedure for Treatment of Female Urinary Incontinence", Scand J Urol Nephrol, vol. 29, No. 1, pp. 75-82, Mar. 1995.
Zimmerman, et al, "Structural and Mechanical Factors Influencing Infarct Scar Collagen Organization", Am. J. Physiol. Heart Circ. Physiol., 278: H194-H200, 2000.

\* cited by examiner

SURGICAL SLINGS

CROSS-REFERENCE TO RELATED APPLICATIONS

This application is a Continuation of, and claims priority to, U.S. patent application Ser. No. 11/360,460, filed Feb. 23, 2006, which, is a continuation-in-part of U.S. application Ser. No. 10/918,123, filed Aug. 13, 2004, which claims the benefit of U.S. Provisional Application No. 60/495,439, filed Aug. 14, 2003, the entire disclosure of each of which is incorporated herein by reference.

TECHNICAL FIELD

The invention generally relates to surgical slings and related methods. More particularly, in one embodiment, the invention relates to surgical slings, such as midurethral slings, that promote growth of collagenous tissue, such as scar tissue, in a well-organized manner.

BACKGROUND INFORMATION

Urinary incontinence affects millions of men and women of all ages in the United States. Stress urinary incontinence (SUI) affects primarily women and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). The result is that there is an insufficient response time to promote urethral closure and, consequently, urine leakage and/or flow results.

A popular treatment of SUI is the use of a sling, which is permanently placed under a patient's bladder neck or midurethra to provide a urethral platform. Placement of the sling limits the endopelvic fascia drop, while providing compression to the urethral sphincter to improve coaptation. Further information regarding sling procedures may be found, for example, in the following: Fred E. Govier et al., "Pubocaginal slings: a review of the technical variables," *Curr. Opin Urol.* 11:405-410, 2001, John Klutke and Carl Klutke, "The promise of tension-free vaginal tape for female SUI," *Contemporary Urol.* pp. 59-73, October 2000; and PCT Patent Publication No. WO 00/74633 A2: "Method and Apparatus for Adjusting Flexible Areal Polymer Implants."

Unfortunately, permanent placement of a sling in a patient's periurethral tissues may cause complications necessitating further surgical intervention. For instance, changes in a patient's body weight and/or anatomy over the course of his/her life, may cause the sling to contact the patient's urethra. This is an undesirable side effect that may result in discomfort and more serious medical problems such as urethral erosion for the patient. As further examples of undesirable side effects, a patient with a sling permanently placed in her periurethral tissues may suffer vaginal mucosal erosion of the vaginal incision that is made during sling implantation, permanent urinary retention, or both. These complications require further surgical intervention to resect the sling. See, e.g., B. G. Volkmer et al. *J. Urol.*, Vol. 169, 2003 February, pp. 570-4.

Due to deficiencies in the prior art, improved surgically implantable slings are needed.

SUMMARY OF THE INVENTION

The invention provides, in one embodiment, a surgically implantable sling (hereinafter a "surgical sling") that includes a pharmaceutical agent or mixture of pharmaceutical agents (hereinafter collectively as an "agent" or "agents"). According to one feature, the surgical sling is, at least in part, biodegradable, while the agent, by stimulating the patient's periurethral tissues, promotes collagenous tissue growth, such as scar tissue, in a well-organized manner surrounding the implanted sling. According to one aspect, when first placed in the patient's periurethral tissues, the biodegradable sling (or biodegradable portion thereof) provides physical support to the patient's urethra. As the biodegradable sling degrades and gradually disappears over time, the patient's tissues form a sling, which includes collagenous tissue, such as scar tissue. This tissue is formed, for example, as a result of stimulating the patient's local tissues with the agent, stimulating the patient's local tissues with biodegradation products of the sling, and so forth. This endogenous/natural collagenous tissue sling provides the requisite support to assist in the correction of the patient anatomy of the local tissues and therefore maintaining continence. According to one feature, the invention reduces the need for a permanent sling, of the type provided by the prior art, by facilitating formation of the natural tissue sling.

In one configuration, a subset of the plurality of biocompatible fibers of the sling is biodegradable.

According to another configuration, the agent includes a growth factor and a hormone, such as estrogen, for facilitating collagenous tissue growth, such as scar tissue. The agent may be, for example, chemically bonded to a subset of the biocompatible fibers, applied as a coating to a subset of the biocompatible fibers, and/or absorbed within the biocompatible fibers. Alternatively, a subset of the plurality of biocompatible fibers may be a blend of the agent and a polymer. The agent may be impregnated into the biocompatible fibers. In another configuration, a subset of the plurality of the biocompatible fibers define a plurality of openings in the surgical sling and a hydrogel containing the agent is applied to the plurality of openings in the sling.

In one configuration, the agent may be associated with a subset of the biocompatible fibers and/or the surgical sling as a whole in any suitable manner.

In one aspect, the invention provides a surgical sling that includes a plurality of biocompatible fibers and an agent associated with a subset of the fibers. According to one feature, the agent promotes collagenous tissue growth, such as scar tissue, in a well-organized manner originating from the patient's tissues at the location of implantation.

According to another embodiment, a surgical sling is provided that includes a plurality of biocompatible and biodegradable fibers with certain surface properties that promote host tissue/cell attachment and further attract and/or promote host tissue growth. In one configuration, the surgical sling includes a plurality of surface properties such as channels to guide the growth of the collagenous tissue such as scar tissue at an anatomical implantation site in the body of the patient. Alternatively, the surgical sling may include one or more through holes for guiding the growth of the collagenous tissue. As another alternative, the surgical sling may be formed from fibers whose diameters promote the growth of the collagenous tissue, inhibit the growth of the collagenous tissue, or both.

According to another embodiment, a surgical sling is provided that includes a plurality of first biodegradable fibers, which are encapsulated by collagenous tissue growth upon implantation. According to one feature, the surgical sling further comprises a plurality of second fibers which are less readily encapsulated by collagenous tissue growth upon implantation than the first fibers.

In another embodiment, the invention provides methods for treating urinary incontinence with a surgical sling according to the invention.

The foregoing and other objects, aspects, features, and advantages of the invention will be apparent from the following illustrative description.

BRIEF DESCRIPTION OF THE DRAWINGS

In the drawings, like reference characters generally refer to the same parts throughout the different views. Also, the drawings are schematic and not necessarily to scale, emphasis instead generally being placed upon illustrating principles of the invention.

DETAILED DESCRIPTION

Figure 1:
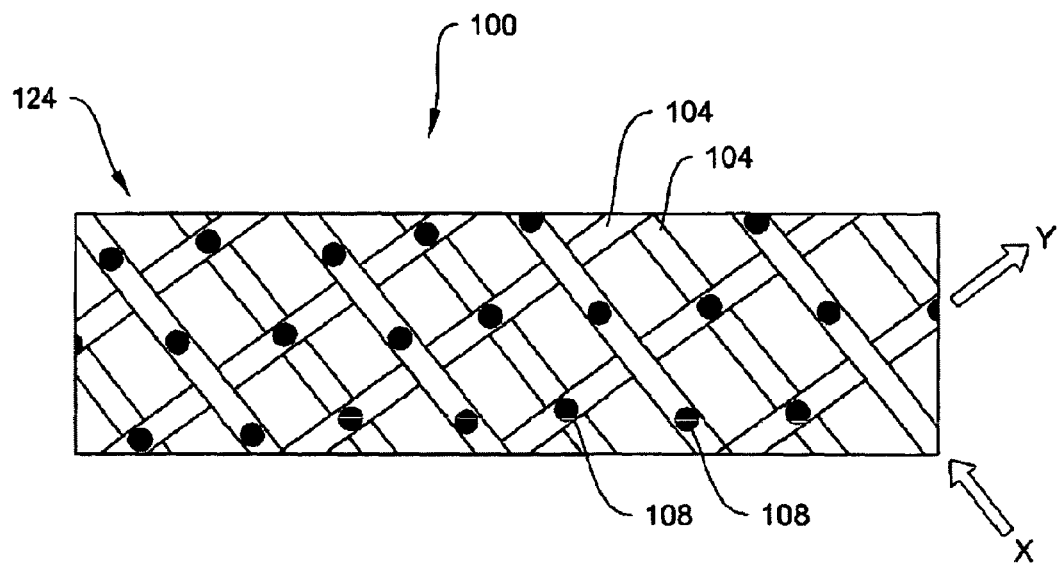
FIG. 1 is a view of a surgical sling according to an illustrative embodiment of the invention.

In general, the invention pertains to surgical slings, and to related methods for implanting the surgical slings at an anatomical site in the body of a patient. According to one feature, the surgical slings and related methods of the invention promote beneficial tissue growth in the region of the implanted sling. According to one illustrative embodiment, the tissue is well organized collagenous tissue, such as scar tissue. The phrase "well organized" is intended to mean that the collagenous tissue growth is not completely random, but instead is in some fashion caused to have some observable organization, direction and/or structure. The organization, direction, and/or structure of the well-organized tissue may be microscopic, such as the arrangement of collagen fibers, macroscopic, such as a collection of smaller tissues formed into an organized bundle, or both microscopic and macroscopic.

The surgical slings of the invention, in various illustrative embodiments, enable a medical operator to control or affect collagenous tissue properties, such as the size, shape, mass, density, organization, direction and/or structure of the tissue. The formation of collagenous tissue is the natural response of the host body toward injury or toward the presence of many foreign materials, such as the material used to form the surgical slings of the invention.

As described in further detail below, according to some features of the invention, by selecting physical properties, such as, the composition, size, shape, texture and/or surface patterning of the sling material, the medical operator can control or affect aspects of collagenous tissue formation.

As also described below in further detail, according to other features of the invention, by selecting chemical properties, such as the composition of the sling material, the agent employed, if any, the agent concentration, and/or the mode of associating the agent with the sling (e.g., chemically bonding the agent to the sling fibers, applying the agent as a coating to the sling fibers, absorbing the agent into sling fibers, blending the agent with the polymer used to form the sling fibers, impregnating the fibers with the agent and/or applying the agent to openings defined by the fibers in the sling), the medical operator can control or affect aspects of collagenous tissue formation.

In certain embodiments the materials forming the surgical slings of the invention, by their chemical nature, form collagenous tissue such as scar tissue upon implantation. In this regard, it is noted that certain biodisintegrable polymers, such as polylactide, polyglycolide, and poly(lactide-co-glycolide), among many others, produce inflammation as they degrade due to pro-inflammatory breakdown products, which leads to the formation of collagenous tissue such as scar tissue. The rate and degree of biodisintegrable polymer breakdown can depend upon a number of factors including monomer content (e.g., choice of monomer or ratio of monomers, if a copolymer), degree of crystallinity, polymer architecture, exposed surface area, and so forth. Thus, in addition to their biodegradable character, such polymers are also selected in certain embodiments of the invention for their ability to promote inflammation and thus collagenous tissue formation.

In certain embodiments, the sling contains sufficient quantities of agent to promote well-organized collagenous tissue growth, such as scar tissue growth. Such agents, referred to herein as "collagenous-tissue-promoting agents," are varied.

Examples of collagenous-tissue-producing agents include, for example, cytokines (i.e., substances made by cells that are used by the same, or other cells, to produce some type of response), endotoxins, chemokines, prostaglandins, lipid mediators, and other mitogens, various natural and synthetic proinflammatory agents and sclerosing agents, and combinations thereof, among others. The agent may also include stem cells or other suitable cells derived from the host patient. These cells may be, for example, fibroblast, myoblast, or other progenitor cells to mature into appropriate tissues.

Further examples of collagenous-tissue-producing agents include, for example, growth factors such as platelet-derived growth factor (PDGF) including platelet-derived growth factor type BB (PDGF-BB), fibroblast growth factor (FGF) including basic fibroblast growth factor (bFGF), transforming growth factors (such as TGF-alpha and TGF-beta), epidermal growth factor (EGF), bone marrow growth factor, insulin-like growth factor (IGF) including insulin-like growth factor 1, vascular endothelium growth factor (VEGF), interleukins such as IL-1-(alpha or beta), IL-8, IL-4, IL6, IL-10 and IL-13, tumor necrosis factor (TNF) such as TNF-alpha, interferons such as INF-gamma, macrophage inflammatory protein-2 (MIP-2), leukotrienes such as leukotriene B4 (LTB4), granulocyte macrophage-colony stimulating factor (GM-CSF), cyclooxygenase-1, cyclooxygenase-2, macrophage chemotactic protein (MCP), inducible nitric oxide synthetase, macrophage inflammatory protein, tissue factor, substance P, Activin/TGF, phosphotyrosine phosphates, N-formyl peptides such as formyl-Met-Leu-Phe (fMLP), second mitochondria-derived activator of caspase (sMAC), activated complement fragments (C5a, C3a), phorbol ester (TPA), steroids including sex steroids, hormones including estrogen, steroid hormones, and other hormones including growth hormones, superoxide, hydrogen peroxide, zymosan, bacterial lipopolysaccharide, chitin, imiquimod, and carrageenan, as well as mixtures thereof, among others.

Proteins employed as agents for the invention, including those described above, include natural and recombinant proteins, and they may be used directly in the slings of the invention as agents, or the slings may be provided with DNA that expresses such proteins in vivo (optionally, in conjunction with a suitable vector).

Further examples of collagenous-tissue-producing agents include sclerosing agents, which may be selected, for example, from the following among others: inorganic materials such as talc, aluminum hydroxide (e.g., in slurry form), sodium hydroxide, silver nitrate, sodium chloride and potassium chloride, as well as organic compounds, including alcohols such as ethanol (e.g., 50% to absolute), acetic acid, trifluoroacetic acid, formaldehyde, dextrose, polyethylene glycol ethers (e.g., polidocanol, also known as laureth 9, polyethylene glycol (9) monododecyl ether, and hydroxypolyethoxydodecane), tetracycline, oxytetracycline, doxycycline, bleomycin, triamcinolone, minocycline, vincristine, iophendylate, tribenoside, sodium tetradecyl sulfate, sodium morrhuate, diatrizoate meglumine, prolamine diatrizoate, alkyl cyanoacrylates such as N-butyl-2-cyanoactyalte and methyl 2-cyanoacrylate, ethanolamine, ethanolamine oleate, bacterial preparations (e.g., corynebacterium and streptococcal preparations such as picibanil) and mixtures of the same, for instance, TES (mixture of 1% tetradecyl sulfate, 32% ethanol, and 0.3% normal saline) and alcoholic solutions of zein (e.g., Ethibloc, which contains zein, alcohol, oleum papaveris, propylene glycol, and a contrast medium), and ethanol/trifluoroacetic acid mixtures, among others.

In various embodiments, the agent may include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

Exemplary steroidal anti-inflammatory therapeutic agents (glucocorticoids) include, but are not limited to, 21-acetoxyprefnenolone, aalclometasone, algestone, amicinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumehtasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol priopionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylaminoacetate, prednisone sodium phosphate, prednisone, prednival, prednylidene, rimexolone, tixocortal, triamcinolone, triamcinolone acetonide, triamcinolone benetonide, triamcinolone hexacetonide, and pharmaceutically acceptable salts thereof.

Exemplary non-steroidal anti-inflammatory therapeutic agents include, but are not limited to, aminoarylcarboxylic acid derivatives such as enfenamic acid, etofenamate, flufenamic acid, isonixin, meclofenamic acid, mefanamic acid, niflumic acid, talniflumate, terofenamate and tolfenamic acid; arylacetic acid derivatives such as acemetacin, alclofenac, amfenac, bufexamac, cimnetacin, clopirac, diclofenac sodium, etodolac, felbinac, fenclofenac, fenclorac, fenclozic acid, fentiazac, glucametacin, ibufenac, indomethacin, isofezolac, isoxepac, lonazolac, metiazinic acid, oxametacine, proglumetacin, sulindac, tiaramide, tolmetin and zomepirac; arylbutyric acid derivatives such as burnadizon, butibufen, fenbufen and xenbucin; arylcarboxylic acids such as clidanac, ketorolac and tinoridine; arylpropionic acid derivatives such as alminoprofen, benoxaprofen, bucloxic acid; carprofen, fenoprofen, flunoxaprofen, flurbiprofen, ibuprofen, ibuproxam, indoprofen, ketoprofen, loxoprofen, miroprofen, naproxen, oxaprozin, piketoprofen, pirprofen, pranoprofen, protizinic acid, suprofen and tiaprofenic acid; pyrazoles such as difenamizole and epirizole; pyrazolones such as apazone, benzpiperylon, feprazone, mofebutazone, morazone, oxyphenbutazone, phenybutazone, pipebuzone, propyphenazone, ramifenazone, suxibuzone and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamine o-acetic acid, salicylsulfuric acid, salsalate and sulfasalazine; thiazinecarboxamides such as droxicam, isoxicam, piroxicam and tenoxicam; others such as .epsilon.-acetamidocaproic acid, s-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole and tenidap; and pharmaceutically acceptable salts thereof.

Exemplary narcotic analgesic therapeutic agents include, but are not limited to, alfentanil, allylprodine, alphaprodine, anileridine, benzylmorphine, bezitramide, buprenorphine, butorphanol, clonitazene, codeine, codeine methyl bromide, codeine phosphate, codeine sulfate, desomorphine, dextromoramide, dezocine, diampromide, dihydrocodeine, dihydrocodeinone enol acetate, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, hydrocodone, hydromorphone, hydroxypethidine, isomethadone, ketobemidone, levorphanol, lofentanil, meperidine, meptazinol, metazocine, methadone hydrochloride, metopon, morphine, myrophine, nalbuphine, narceine, nicomorphine, norlevorphanol, normethadone, normorphine, norpipanone, opium, oxycodone, oxymorphone, papavereturn, pentazocine, phenadoxone, phenazocine, pheoperidine, piminodine, piritramide, proheptazine, promedol, properidine, propiram, propoxyphene, rumifentanil, sufentanil, tilidine, and pharmaceutically acceptable salts thereof.

Exemplary non-narcotic analgesic agents that maybe combined with the sling 100 include, but are not limited to, aceclofenac, acetaminophen, acetaminosalol, acetanilide, acetylsalicylsalicylic acid, alclofenac, alminoprofen, aloxiprin, aluminum bis(acetylsalicylate), aminochlorthenoxazin, 2-amino-4-picoline, aminopropylori, aminopyrine, ammonium salicylate, amtolmetin guacil, antipyrine, antipyrine salicylate, antrafenine, apazone, aspirin, benorylate, benoxaprofen, benzpiperylon, benzydamine, bermoprofen, brofenac, p-bromoacetanilide, 5-bromosalicylic acid acetate, bucetin, bufexamac, burnadizon, butacetin, calcium acetylsalicylate, carbamazepine, carbiphene, carsalam, chloralantipyrine, chlorthenoxazin(e), choline salicylate, cinchophen, ciramadol, clometacin, cropropamide, crotethamide, dexoxadrol, difenamizole, diflunisal, dihydroxyaluminum acetylsalicylate, dipyrocetyl, dipyrone, emorfazone, enfenamic acid, epirizole, etersalate, ethenzamide, ethoxazene, etodolac, felbinac, fenoprofen, floctafenine, flufenamic acid, fluoresone, flupirtine, fluproquazone, flurbiprofen, fosfosal, gentisic acid, glafenine, ibufenac, imidazole salicylate, indomethacin, indoprofen, isofezolac, isoladol, isonixin, ketoprofen, ketorolac, p-lactophenetide, lefetamine, loxoprofen, lysine acetylsalicylate, magnesium acetylsalicylate, methotrimeprazine, metofoline, miroprofen, morazone, morpholine salicylate, naproxen, nefopam, nifenazone, 5' nitro-2' propoxyacetanilide, parsalmide, perisoxal, phenacetin, phenazopyridine hydrochloride, phenocoll, phenopyrazone, phenyl acetylsalicylate, phenyl salicylate, phenyramidol, pipebuzone, piperylone, prodilidine, propacetamol, propyphenazone, proxazole, quinine salicylate, ramifenazone, rimazolium metilsulfate, salacetamide, salicin, salicylamide, salicylamide o-acetic acid, salicylsulfuric acid, salsalte, salverine, simetride, sodium salicylate, sulfamipyrine, suprofen, talniflumate, tenoxicam, terofenamate, tetradrine, tinoridine, tolfenamic acid, tolpronine, tramadol, viminol, xenbucin, zomepirac, and pharmaceutically acceptable salts thereof.

Exemplary local anesthetic therapeutic agents include, but are not limited to, ambucaine, amolanone, amylocalne hydrochloride, benoxinate, benzocaine, betoxycaine, biphenamine, bupivacaine, butacaine, butaben, butanilicaine, butethamine, butoxycaine, carticaine, chloroprocaine hydrochloride, cocaethylene, cocaine, cyclomethycaine, dibucaine hydrochloride, dimethisoquin, dimethocaine, diperadon hydrochloride, dyclonine, ecgonidine, ecgonine, ethyl chloride, beta-eucaine, euprocin, fenalcomine, fomocaine, hexylcaine hydrochloride, hydroxytetracaine, isobutyl p-aminobenzoate, leucinocaine mesylate, levoxadrol, lidocaine, mepivacaine, meprylcaine, metabutoxycaine, methyl chloride, myrtecaine, naepaine, octacaine, orthocaine, oxethazaine, parethoxycaine, phenacaine hydrochloride, phenol, piperocaine, piridocaine, polidocanol, pramoxine, prilocalne, procaine, propanocaine, proparacaine, propipocaine, propoxycaine hydrochloride, pseudococaine, pyrrocaine, ropavacaine, salicyl alcohol, tetracaine hydrochloride, tolycaine, trimecaine, zolamine, and pharmaceutically acceptable salts thereof.

Exemplary antispasmodic therapeutic agents include, but are not limited to, alibendol, ambucetamide, aminopromazine, apoatropine, bevonium methyl sulfate, bietamiverine, butaverine, butropium bromide, n-butylscopolammonium bromide, caroverine, cimetropium bromide, cinnamedrine, clebopride, coniine hydrobromide, coniine hydrochloride, cyclonium iodide, difemerine, diisopromine, dioxaphetyl butyrate, diponium bromide, drofenine, emepronium bromide, ethaverine, feclemine, fenalamide, fenoverine, fenpiprane, fenpiverinium bromide, fentonium bromide, flavoxate, flopropione, gluconic acid, guaiactamine, hydramitrazine, hymecromone, leiopyrrole, mebeverine, moxaverine, nafiverine, octamylamine, octaverine, oxybutynin chloride, pentapiperide, phenamacide hydrochloride, phloroglucinol, pinaverium bromide, piperilate, pipoxolan hydrochloride, pramiverin, prifinium bromide, properidine, propivane, propyromazine, prozapine, racefemine, rociverine, spasmolytol, stilonium iodide, sultroponium, tiemonium iodide, tiquizium bromide, tiropramide, trepibutone, tricromyl, trifolium, trimebutine, n,n-ltrimethyl-3,3-diphenylpropylamine, tropenzile, trospium chloride, xenytropium bromide, and pharmaceutically acceptable salts thereof.

Two particular therapeutic agents which may be employed in various illustrative embodiments of the invention are: (a) ketorolac and pharmaceutically acceptable salts thereof (e.g., the tromethamine salt thereof, sold under the commercial trade name Toradol®) and (b) 4-diethylamino-2-butynylphenylcyclohexylglycolate and pharmaceutically acceptable salts thereof (e.g., 4-diethylamino-2-butynylphenylcyclohexylglycolate hydrochloride, also known as oxybutynin chloride, sold under the commercial trade name Ditropan®).

In certain embodiments, the sling is at least partially biodegradable. In this regard, it is believed that on the order of approximately 60% of all patients from whom surgical slings are removed (e.g., due to complications such as those previously discussed) nevertheless remain continent after this procedure as a result of newly formed scar tissue, which plays a key role in supporting proper urethral function. Thus, in some embodiments, the surgical slings of the invention are designed to support the urethral function initially through their mechanical characteristics. After implantation, the implanted slings stimulate the host to generate collagenous tissue to take over the required function, and the biodegradable materials of the slings are broken down. This newly generated tissue may take on various forms, depending to the configuration and composition of the sling, for example, corresponding to scar tissue in the form of multiple collagen bundles or "artificial tendons." Being living tissue, this newly generated tissue may respond to the needs of the host. (As a specific example, the collagenous tissue formed after tendon injury is known to reorient itself along the long direction of the tendon, which coincides with the direction of tensile stress.)

Exemplary biodegradable materials suitable for forming surgical slings (or portions thereof) in accordance with the invention the practice of the invention include, but are not limited to, natural tissue such as human tissue and decellularized plant and animal tissue. Human tissues may be derived, for example, from human cadaveric or engineered human tissue. Animal tissues may be derived, for example, from porcine, ovine, bovine, and equine tissue sources, among many others.

Additional exemplary biodegradable materials include biodegradable polymers, which may be natural, synthetic or a combination of both. They may be homopolymers or copolymers. They may take on a variety of architectures, including linear, cyclic, branched and network architectures, among others. "Branched architectures" as the term is used herein, include star-shaped architectures (e.g., architectures in which three or more arms emanate from a single branch point), comb architectures (e.g., architectures having a main chain and a plurality of side chains) and dendritic architectures (e.g., arborescent and hyperbranched polymers), among others. Blends of differing biodegradable polymers may also be used. The sling material may also be made of a combination of biodegradable polymers and tissues.

Specific examples of natural biodegradable polymers and their derivatives include polysaccharides such as hyaluronic acid, chitosan, hydroxypropylmethylcellulose; and poly (amino acids) and proteins, such as gelatin, collagen, fibronectin, laminin, elastin, and mixtures thereof. Thus, many natural biodegradable polymers for the slings of the invention are components of the extracellular matrix.

Additional exemplary biodegradable polymers that may be used in accordance with the invention include polyesters, polyanhydrides, and amino-acid-based polymers, among others, for instance, homopolymers and copolymers (and their derivatives) which are formed from (or have the appearance of being formed from) one or more of the following monomers: (a) alpha-hydroxy acids such as glycolic acid (also known as glycolide in dimer form), D-lactic acid and L-lactic acid (also known as D- and L-lactide in dimer form), D-malic acid and L-malic acid, among others; (b) other hydroxyl acids, including beta-, gamma-, delta-, and epsilon-hydroxy acids, as well as hydroxy acids having multiple hydroxyl groups, among others, for example, hydroxybutyric acids such as beta-hydroxybutyric acid (also known as 3-hydroxybutyric acid), gamma-hydroxybutyric acid (also known as 4-hydroxybutyric acid, and as gamma-butyrolactone in its closed ring form), hydroxyvaleric acids such as beta-hydroxyvaleric acid (also known as 3-hydroxyvaleric acid), gamma-hydroxyvaleric acid (also known as 4-hydroxyvaleric acid), delta-hydroxyvaleric acid (also known as 5-hydroxyvaleric acid, and as delta-valerolactone in its closed ring form), hydroxycaproic acids such as epsilon-hydroxycaproic acid (also known as 6-hydroxycaproic acid, or as epsilon-caprolactone in its closed ring form), as well as D-gluconic acid and L-gluconic acid, among others; (c) ester-ethers, for instance, alkyl-substituted and unsubstituted dioxanones, such as p-dioxanone (1,4-dioxan-2-one), substituted 1,4-dioxan-2-ones (e.g., alkyl substituted 1,4-dioxan-2-ones such as 6,6-dimethyl-1,4-dioxan-2-one), substituted-1,4-dioxane-2,5-diones (e.g., substituted 1,4-dioxane-2,5-diones such as 3-methyl-1,4-dioxane-2,5-dione, 3,3-diethyl-1,4-dioxan-2,5-dione and 3,6-substituted-1,4-dioxane-2,5-diones), alkyl-substituted and unsubstituted dioxepanones, including 1,4-dioxepan-2-one (including its dimmer from) and 1,5-dioxepan-2-one, among others; (d) epoxy-esters such as trimethylene carbonate (also known as 1,3-dioxan-2-one) and ethylene carbonate (also known as 1,3-dioxolan-2-one), among others; and (e) diacids including alpha,omega-bis-(carboxy)alkanes and alpha,omega-bis-(carboxy)alkenes, for instance, maleic acid (cis-1,2-ethylenedicarboxylic acid), fumaric acid (trans-1,2-ethylenedicarboxylic acid), adipic acid, suberic acid, sebacic acid, and dodecanedioic acid, aromatic diacids including bis(p-carboxyphenoxy)methane, and alpha,omega-bis-(p-carboxyphenoxy)alkanes such as 1,3-bis (p-carboxyphenoxy)propane and 1,6-bis(p-carboxyphenoxy)hexane, among others; and (f) amino acid based polymers include tyrosine-based polyarylates (e.g., copolymers of a diphenol and a diacid linked by ester bonds, with diphenols selected, for instance, from ethyl, butyl, hexyl, octyl and bezyl esters of desaminotyrosyl-tyrosine and diacids selected, for instance, from succinic, glutaric, adipic, suberic and sebacic acid), tyrosine-based polycarbonates (e.g., copolymers formed by the condensation polymerization of phosgene and a diphenol selected, for instance, from ethyl, butyl, hexyl, octyl and bezyl esters of desaminotyrosyl-tyrosine), and leucine and lysine-based polyester-amides.

Further biodegradable polymers can be selected from the following, among many others: polymers and copolymers of lactide and glycolide such as poly(L-lactide) (PLLA), poly (D,L-lactide) (PLA), polyglycolic acid [polyglycolide (PGA)], poly(L-lactide-co-D,L-lactide) (PLLA/PLA), poly (L-lactide-co-glycolide) (PLLA/PGA), poly(D,L-lactide-co-glycolide) (PLA/PGA), poly(glycolide-co-trimethylene carbonate) (PGA/PTMC), poly(lactide-co-trimethylene carbonate), poly(lactide-co-delta-valerolactone), poly(L-lactide-co-beta-malic acid), poly(D,L-lactide-co-caprolactone) (PLA/PCL), and poly(glycolide-co-caprolactone) (PGA/PCL), polyethylene oxide (PEO), polydioxanone (PDS), polypropylene fumarate, polydepsipeptides, poly(ethyl glutamate-co-glutamic acid), poly(tert-butyloxy-carbonylmethyl glutamate), caprolactone and vaerolactone polymers and copolymers such as polycaprolactone (PCL), poly(delta-valerolactone) and poly(caprolactone-co-butylacrylate), hydroxybutyrate polymers and copolymers such as polyhydroxybutyrate (PHBT) and poly(beta-hydroxybutyrate-co-beta-hydroxyvalerate), polyphosphazenes, poly(phosphate esters), anhydride polymers and copolymers such as poly (adipic anhydride), poly(suberic anhydride), poly(sebacic anhydride), poly(dodecanedioic anhydride), poly(maleic anhydride), poly[1,3-bis(p-carboxyphenoxy)methane anhydride] and poly[alpha,omega-bis(p-carboxyphenoxy)alkane anhydrides] such as poly[1,3-bis(p-carboxyphenoxy)propane anhydride] and poly[1,3-bis(p-carboxyphenoxy)hexane anhydride], maleic anhydride copolymers, poly[1,3-bis(p-carboxyphenoxy)propane-co-sebacic acid], and poly(sebacic acid-co-fumaric acid); carbonates polymers and copolymers such as poly(trimethylene carbonate), polyiminocarbonates, and poly[(dimethyl-trimethylene carbonate)-co-(trimethylene carbonate)], e.g., poly[(97.5% dimethyl-trimethylene carbonate)-co-(2.5% trimethylene carbonate)], cyanoacrylates, poly-D-gluconate, poly-L-gluconate, poly-D,L-gluconate, polyorthoesters such as those synthesized by condensing 2,2-diethoxytetrahydrofuran and di-alcohols, and tyrosine-based polymers such as poly(desaminotyrosyl-tyrosine ethyl ester adipate) or poly(DTE adipate), poly(desaminotyrosyl-tyrosine hexyl ester succinate) or poly(DTH succinate), poly(desaminotyrosyl-tyrosine ethyl ester carbonate) or poly(DTE carbonate), poly(desaminotyrosyl-tyrosine butyl ester carbonate) or poly(DTB carbonate), poly (desaminotyrosyl-tyrosine hexyl ester carbonate) or poly (DTH carbonate), and poly(desaminotyrosyl-tyrosine octyl ester carbonate) or poly(DTO carbonate).

In certain embodiments, all or a portion of the materials forming the slings of the invention consist of or contain one or more species that promote cellular attachment. In certain other embodiments, the surfaces of all or a portion of the materials forming the slings of the invention are provided with one or more species that promote cellular attachment (e.g., by coating, covalent attachment, etc.).

Species that promote cellular attachment may be selected, for example, from suitable members of the following (or active portions thereof), among others: extracellular materials such as submucosa, bone marrow ECM, and basement membrane; various components of extracellular materials, including fibrous materials and ground substance (e.g., glycosaminoglycans, proteoglycans, and glycoproteins), for instance, collagen, laminin, elastin, fibronectin, tenascin, perlecan, aggrecan, heparin sulfate, hyaluron, dermatan sulfate, keratin sulfate, and chrondroitin sulfate, among others, ankyrins, cadherins, members of the immunoglobulin superfamily (which includes a wide array of molecules, including NCAMs, ICAMs, VCAMs, and so forth), selectins (L-, E- and P-subclasses), connexins, mucoadhesives, entactin, fibrin, vimentin, glycolipids, glycophorin, spektrin, von Willebrand factor, vinculin, vitronectin, and peptides and proteins containing various peptide attachment sequences including species containing RGD tripeptide, which has been identified to be responsible for some of the cell adhesion properties of fibronectin, laminin, collagen I, collagen IV, thrombospondin, and tenascin, including, for example, the GRGDY pentapeptide. More information on these and other peptides can be found in U.S. Pat. No. 6,156,572, U.S. Patent Application No. 2003/0087111 and M. Tirrell et al., "The role of surface science in bioengineered materials" *Surface Science* 500 (2002) 61-83.

Many of the above species that promote cellular attachment exhibit highly selective interactions, such as ligand-receptor or antibody-antigen type interactions. Others, including various mucoadhesives, exhibit more broad-based adhesion. Mucoadhesives commonly have free carboxylic acid or other anionic groups (e.g., sulfonic acid groups). Specific examples of mucoadhesives, non-exclusive of the mucoadhesives listed in the prior paragraph, include the following: acrylic acid polymers and copolymers (e.g., carbomer and derivatives such as carbopol and polycarbophil), poloxamers, celluloses such as methyl cellulose, polyvinyl alcohol, carboxymethyl cellulose and salts thereof, carboxyethyl cellulose and salts thereof, hyroxypropylmethyl cellulose, chitin, chitosan, chondroitin, hyaluronic acid and other glycosaminoglycans, pectin, gelatin, gums such as guar gum, xanthan gum, arabic gum, and tracanth, agarose, and alginates.

It should be noted that although surgical slings for treating urinary incontinence are described in the illustrative embodiments, the invention may be employed, generally, with any suitable medical implant, specifically, with any surgical sling. For example, the sling may be a mesh.

According to various illustrative configurations, the surgical sling may be, for example, in the range of about 5 cm to about 50 cm in length, and about 0.5 cm to about 3 cm wide, though larger or smaller slings may be employed to suit the size of the patient and/or the application. The thickness of the surgical sling may be uniform over the entire sling, or the thickness may vary at one or more different locations. According to various illustrative embodiments, the thickness of the surgical sling ranges, for example, from about 0.01 cm to about 0.2 cm, and in one embodiment is about 0.08 cm.

The surgical sling of the invention may have any suitable size or shape configuration and may include any complimentary features. By way of example, the surgical sling may be rectangular or substantially rectangular, trapezoidal, hexagonal, octagonal or elliptical in shape, as may be suitable for its intended location at a particular anatomical site. The sling may also have a forked configuration at one or both ends. In some illustrative embodiments, the edges of the sling may be linear in nature (i.e., not tanged) or may have V-shaped projections or be frayed (i.e., tanged) at the edge. In certain illustrative embodiments, the surgical sling may have apertures, of any suitable shape and size, for example, round, square, diamond-shaped, or triangular. In other illustrative embodiments, at least one of the sides of the surgical sling is textured. The textured or irregular surface acts, for example, to enhance tissue growth into the sling and/or aid in stabilization of the sling in the tissue through frictional forces, among other purposes. Without limitation, examples of various sling configurations that may be with illustrative embodiments of the invention are disclosed in U.S. Ser. No. 10/092, 872, entitled "Medical slings," U.S. Ser. No. 10/640,838, entitled "Medical implant," U.S. Ser. No. 10/641,170, entitled "Medical slings," and U.S. Ser. No. 10/641,192, entitled "Medical slings," the entire contents of all of which are incorporated herein by reference.

According to another illustrative embodiment, the surgical sling of the invention includes a tensioning mechanism, for example, for limiting the stretchability of the surgical sling, for aiding in the application of even tension along the length of the sling, and/or for aiding in preventing the surgical sling from becoming misshapen. Such a tensioning mechanism may be embedded in the sling material and/or may be made, for example, from resorbable or non-resorbable suture material. The tensioning device may be substantially linear or coiled. Examples of resorbable suture materials include, without limitation, polylactic acid (PLA), polyglycolic acid (PGA), and poly-L-lactic acid (PLLA). Further resorbable suture materials may be selected from the biodegradable materials described above, among others. Examples of non-resorbable suture materials include, without limitation, polypropylene (PP) and polybutester. Without limitation, examples of tensioning mechanisms that may be employed with illustrative embodiments of the invention are disclosed in U.S. Pat. No. 6,666,817, entitled "Expandable surgical implants and methods of using them," U.S. Pat. No. 6,669, 706, entitled "Thin soft tissue surgical support mesh," U.S. Pat. No. 6,375,662, entitled "Thin soft tissue surgical support mesh," U.S. Pat. No. 6,042,592, entitled "Thin soft tissue surgical support mesh," the entire contents of all of which are incorporated herein by reference.

According to other illustrative embodiments, the surgical sling of the invention may be employed as part of a sling assembly, including, for example, a sleeve for enclosing at least a portion of the surgical sling, and terminating in any suitable configuration or structure such as loops, apertures, male or female connectors, guide tubes, and the like. Additionally, the surgical sling of the invention may be employed with any suitable delivery system. Such delivery systems include, for example, those delivery systems configured for supra-pubic, pre-pubic, transvaginal, and/or transobturator procedures. Without limitation, examples of sling assemblies, delivery devices and implantation approaches that may employ illustrative embodiments of the invention are disclosed in U.S. Ser. No. 10/015,114, entitled "Devices for minimally invasive pelvic surgery," U.S. Ser. No. 10/774,826, entitled "Devices for minimally invasive pelvic surgery," U.S. Ser. No. 10/093,398, entitled "System for implanting an implant and method thereof," U.S. Ser. No. 10/093,498, entitled "System for implanting an implant and method thereof," U.S. Ser. No. 10/093,371, entitled "System for implanting an implant and method thereof," U.S. Ser. No. 10/093,424, entitled "System for implanting an implant and method thereof," U.S. Ser. No. 10/093,450, entitled "System for implanting an implant and method thereof," U.S. Ser. No. 10/094,352, entitled "System for implanting an implant and method thereof," U.S. Ser. No. 10/631,364, entitled "Bioabsorbable casing for surgical sling assembly," U.S. Ser. No. 10/641,376, entitled "Spacer for sling delivery system," U.S. Ser. No. 10/641,487, entitled "Systems, methods and devices relating to delivery of medical implants," U.S. Ser. No. 10/642,395, entitled "Systems, methods and devices relating to delivery of medical implants," U.S. Ser. No. 10/642,397, entitled "Systems, methods and devices relating to delivery of medical implants," U.S. Ser. No. 10/832,653, entitled "Systems and methods for sling delivery and placement," U.S. Provisional Application No. 60/569,300, entitled "Systems and methods for delivering a medical implant to an anatomical location in a patient," and U.S. Provisional Application No. 60/508,600 entitled "Systems and methods for delivering a medical implant to an anatomical location in a patient," the entire contents of all of which are incorporated herein by reference.

Turning to the illustrative drawings, FIG. 1 depicts a view showing a first side 124 of a surgical sling 100 according to an illustrative embodiment of the invention. The sling 100 is generally rectangular in shape and flat, or sheet-like, with a first side 124, which is seen in this view, and a second side 126, which cannot be seen in this view. As shown, the sling 100 is manufactured from a plurality of fibers 104, and includes at least one agent 108. The fibers used to weave the sling sheet may extend in at least two directions, i.e., X- and Y-directions, which may or may not be perpendicular to one another. The fibers extending in the different directions may be the same or they may be different in terms of chemical composition, the agent loaded, if any, physical dimensions, such as diameter, and surface properties to suit the needs of promoting organized tissue formation, such as guiding collagenous tissue growth, particularly scar tissue, in one preferred direction.

The fibers 104 of the sling 100 are made of a biocompatible material and may be, for example, knitted or woven to form the sling 100. As used herein, the term "biocompatible" refers to a material that is substantially non-toxic and that does not induce a significantly adverse effect on the patient's health. According to one aspect, at least a portion of the sling 100 is biodegradable. For example, in one illustrative embodiment, the fibers 104 are biodegradable. However, this need not be the case. In other illustrative embodiments, only some of the fibers 104 are biodegradable, or only a section of the surgical sling 100, such as, for example, a mid-length section, is biodegradable.

For example, in one embodiment, only a corresponding mid-length section of the fibers 104 are biodegradable. In some illustrative embodiments, the fibers 104 in the other sections of the surgical sling 100 are made of a non-bioabsorbable material. In some such embodiments, the biodegradable mid-length section has a length of about 1 mm to about 25 mm, about 5 mm to about 15 mm, or, most preferably, about 5 mm to about 10 mm.

As indicated above, collagenous-tissue-promoting agent 108, when supplied to patient's tissues in a pharmaceutically acceptable amount, promote well-organized collagenous tissue growth, such as scar tissue growth, preferably, in large quantities. According to one feature, the agent 108 may or may not block or delay the biodegradability of the sling 100. This may be controlled by selecting different methods to load the agent onto the sling fibers. According to the illustrative embodiment of FIG. 1, the agent 108 includes a tissue-growth-promoting agent, but any suitable agent may be employed, including those described above.

In various illustrative embodiments, agent 108 may be supplied which include one or more therapeutic agents. The therapeutic agents may be, for example, anti-inflammatory agents, including steroidal and non-steroidal anti-inflammatory agents, analgesic agents, including narcotic and non-narcotic analgesics, local anesthetic agents, antispasmodic agents, growth factors, gene-based therapeutic agents, and combinations thereof.

The agent 108 may be associated with the sling 100 in a variety of manners. For example, referring again to FIG. 1, the agent 108 may be chemically or physically attached to the surface of one or more of the biocompatible fibers 104. In one illustrative embodiment, the surface of the biocompatible fibers 104 and the agent 108, for example, in solution, have complementary ionic charges. As such, when placed on the fibers 104, the agent 108 ionically bonds to the surface of the fibers 104.

In another illustrative embodiment, before application of the agent 108, a coating is applied to the surface of the fibers 104. For example, a hydrophilic or hydrophobic coating may be applied to the surface of the fibers 104. The hydrophilic or hydrophobic coating then absorbs a hydrophilic or hydrophobic agent 108, respectively, to the surface of the fibers 104. In yet another embodiment, the hydrophilic or hydrophobic coating and the hydrophilic or hydrophobic agent 108, respectively, are mixed together to form a single coating and then applied to the surface of the fibers 104. Alternatively, in another illustrative embodiment, the agent 108 is in the form of, for example, a paste or a gel. The agent 108 is itself applied as a coating to the surface of the fibers 104 and held in place by, for example, various non-covalent binding forces. In other illustrative embodiments, any suitable methodology for associating the agent 108 with the fibers 104, such that the agent 108 can leach to tissue in the region of the implanted sling 100, may be employed.

Figure 2:
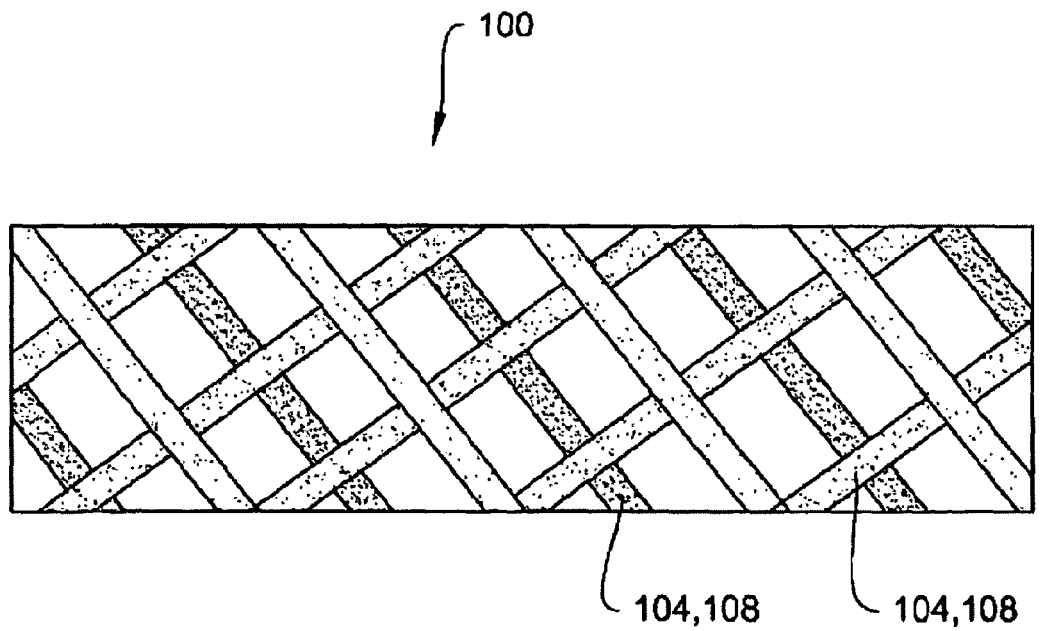
FIG. 2 is a view of a surgical sling according to another illustrative embodiment of the invention.

FIG. 2 depicts a surgical sling 100 according to another illustrative embodiment of the invention. As shown, rather than being attached to the surface of the biocompatible fibers 104, as in FIG. 1, the agent 108 is integrally combined with the fibers 104. This integral combination may be achieved in a variety of ways. For example, in one illustrative embodiment, the agent 108 is initially blended with a polymer. The agent 108/polymer blend is then used to fabricate the fibers 104. As another example, in another illustrative embodiment, a preexisting fiber 104 is impregnated the agent 108. The fibers 104 containing the agent 108 may be knitted or weaved, for example, to construct the sling 100. In another illustrative embodiment, the agent 108 loaded fiber is knitted or weaved into the fibers extending in one direction, for example, the X direction, to promote guided/oriented tissue growth/attachment. In one illustrative embodiment, the agent 108 is impregnated into the finished sling or mesh. For example, in an illustrative embodiment, the fibers 104 are made of a wettable material. The agent 108, for example, in solution, is then applied to and absorbed into the fibers 104.

Figure 3:
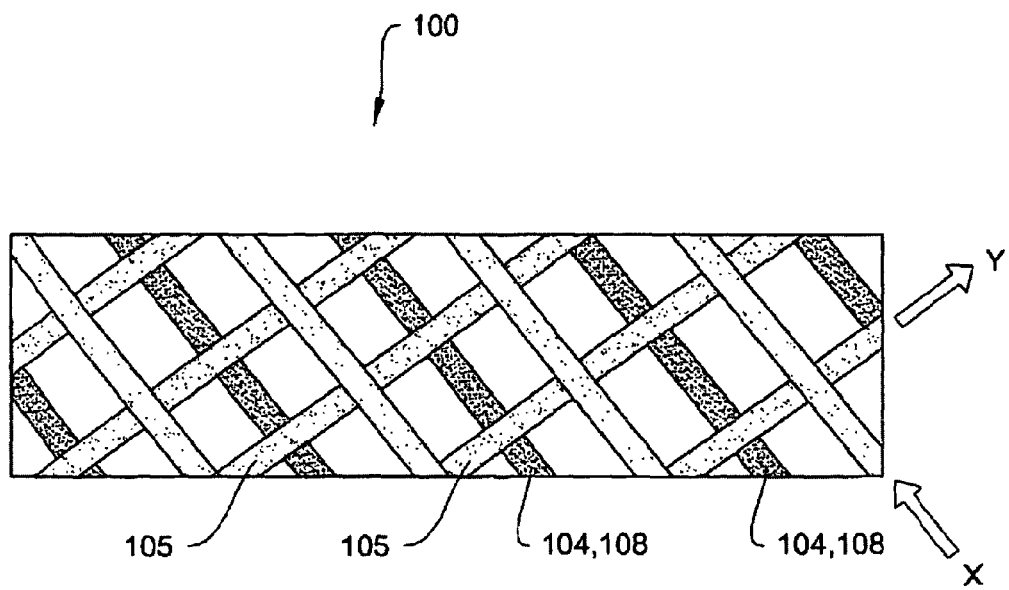
FIG. 3 is a view of a surgical sling according to another illustrative embodiment of the invention, showing a weave made of more than one type of material.

FIG. 3 depicts another illustrative embodiment of the surgical sling 100. In this example, the sling may be made of two or more types of fibers knitted or woven together to construct the sling 100. The fibers 104 and the fibers 105 may have different chemical characteristics from each other, different physical characteristics from each other, or both. The fibers 104 extend in direction X relative to the orientation of the surgical sling 100 and the fibers 105 extend in direction Y, different from the direction of the fibers 104, relative to the orientation of the surgical sling 100. In one illustrative embodiment, the fibers 104 may be fabricated with an agent 108, while the fibers 105 may be fabricated with the same agent 108, a different agent 108, or with no agent. In another embodiment, the differences in the physical characteristics of the fibers 104 and 105, with or without agent, guide the formation of well-organized collagenous tissue such as scar tissue. In one embodiment, the fibers 104 have surface features that promote the growth of well-organized collagenous tissue such as scar tissue, whereas the fibers 105 may or may no have such features. In a yet another embodiment, these surface structures are combined with the presence of the agent 108.

Figure 8A:
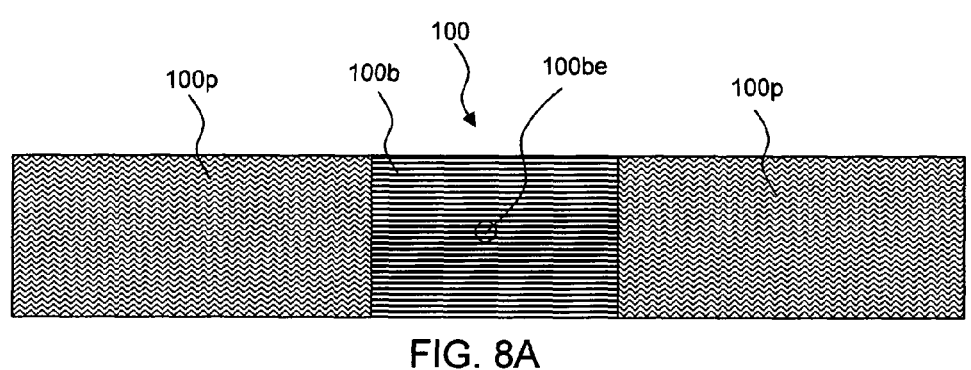
FIG. 8A is a view of a sling according to another alternative illustrative embodiment of the invention.
Figure 8B:
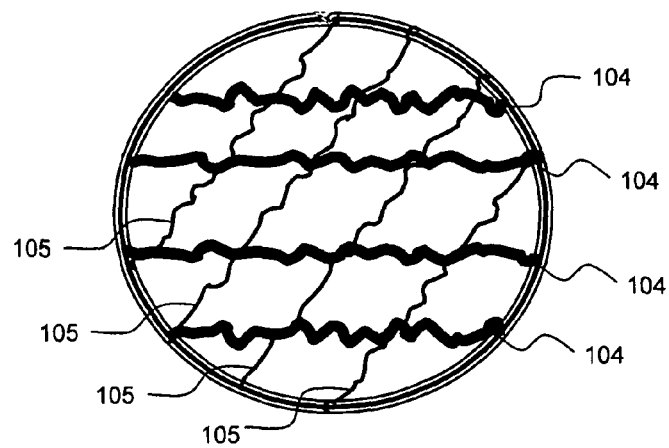
FIG. 8B is an expanded view of a portion of FIG. 8A.

FIGS. 8A and 8B depict another illustrative embodiment of the surgical sling 100. In this example, sling 100 contains both biodegradable 100b and permanent 100p portions. FIG. 8B is a schematic enlarged view of a portion 100be of biodegradable region 100b of FIG. 8A. As seen from this drawing, region 100b of FIG. 8A includes longitudinal fibers 104 and holding fibers 105. The longitudinal fibers 104 in this embodiment are adapted to promote collagenous tissue formation.

In an illustrative embodiment, the longitudinal fibers 104 are adapted to be encapsulated in collagenous tissue, forming what may be termed as a "micro scar." In one aspect, these tiny micro scars are inter-linked to form the bundles of fibers and those bundles are further stabilized by the permanent holding fibers to form a macroscopically organized collagen bundles or "artificial tendons".

In an illustrative embodiment, by selecting a suitable biodegradable material for the fibers 104, the fibers themselves stimulate moderate inflammation upon biodegradation, and therefore scar formation surrounding the fiber. The newly formed collagenous tissue will then take over the load gradually, as the fiber degrades. Biodegradation may occur over a period of three to six months, among other time frames, as described below.

Preferably, the longitudinal fibers 104 in this embodiment are adapted to promote collagenous tissue formation to a greater degree than do the holding fibers 105. Preferential collagenous tissue formation may be achieved via the chemical characteristics of the sling 100, the physical characteristics of the sling 100, or both.

For instance, preferential collagenous tissue formation may be achieved in some embodiments, by providing the holding fibers 105 in a substantially lower density than the longitudinal fibers 104 (e.g., having a fiber-to-fiber spacing that is 2 to 50 to 10 to 25 to 50 to 100 or more times that between the longitudinal fibers 104). In some embodiments, the holding fibers 104 may be dispensed with entirely.

As an alternative to (or in addition to) varying fiber density, in certain illustrative embodiments, the fibers 104, 105 are adapted such that collagenous tissue formation occurs to a greater extent along the longitudinal fibers 104, relative to the holding fibers 105.

As a specific example, research by J. E. Sanders and others with various fibers has revealed that microfiber diameter influences fibrous capsule formation to a greater degree than various other factors, including fiber composition or fiber surface charge. In particular, they noted reduced fibrous capsule thicknesses for small fibers (<6 µm diameter) as compared with larger fibers (i.e., fibers ranging from ~6 to ~27 µm, depending on the study), with many of the small fibers displaying no capsule and no sign of a foreign-body reaction. See J. E. Sanders et al., "Relative influence of polymer fiber diameter and surface charge on fibrous capsule thickness and vessel density for single-fiber implants," *Biomed Mater Res A*. 2003 Jun. 15; 65(4): 462-7, J. E. Sanders et al., "Tissue response to single-polymer fibers of varying diameters: evaluation of fibrous encapsulation and macrophage density," *J Biomed Mater Res*. 2000 October; 52(1): 231-7; J. E. Sanders et al., Tissue response to microfibers of different polymers: polyester, polyethylene, polylactic acid, and polyurethane," *J Biomed Mater Res*. 2002 November; 62(2): 222-7; J. E. Sanders et al., "Polymer microfiber mechanical properties: a system for assessment and investigation of the link with fibrous capsule formation," *J Biomed Mater Res A*. 2003 Dec. 15; 67(4): 1412-6.

Thus, the diameter of the fibers 104, 105 of FIG. 8B may be controlled such that that such that fibrous encapsulation is preferentially promoted along the longitudinal fibers 104, relative to the holding fibers 105. For example, the longitudinal fiber may have diameters greater than 1 µm (e.g., about 1 µm to 5 µm to 10 µm to 25 µm to 50 µm to 100 µm, for instance, about 10 µm) while the holding fibers may have diameters less than 10 µm (e.g., about 100 nm to 250 nm to 500 nm to 1 µm to 2.5 µm to 5 µm to 10 µm, for instance about 1 µm). Fiber surface and spacing may also have an effect upon tissue formation and thus may be optimized for enhanced tissue formation on longitudinal fibers 104, inhibited tissue formation on holding fibers 105, or both.

As another example, longitudinal fibers 104 may be provided with longitudinal grooves or other surface topography effective to promote well-organized collagenous tissue growth along the fibers, whereas the holding fibers 105 are not.

As an alternative to (or in addition to) varying fiber density, diameter, morphology and/or spacing, tissue formation may be enhanced for the longitudinal fibers 104 relative to the holding fibers 105 by using fiber compositions that promote collagenous tissue growth along the longitudinal fibers 104, by using fiber characteristics that inhibit collagenous tissue growth (e.g., surface smoothness as well as hydrophilic vs. hydrophobic surfaces, etc.) along the holding fibers 105, or both.

For instance, the longitudinal fibers 104 may be formed from a biodegradable material that promotes collagen tissue production to a greater degree than the material used to form the spacer fibers 105. For example, the longitudinal fibers 104 may be formed from a polymer which provokes an inflammation response, whereas the spacer fibers 105 may be formed from a polymer that does not. As another example, the longitudinal fibers 104 may be formed from a polymer promotes cellular attachment, whereas the spacer fibers 105 may be formed from a polymer that does not.

As another example, fiber composition can be differentiated by providing the longitudinal fibers 104 with collagenous-tissue-promoting agents, by providing the spacer fibers 105 with collagenous-tissue-inhibiting agents, or both. Such agents may be provided, within the matrix forming the longitudinal fibers 104, at the surface of the longitudinal fibers 104, within the matrix forming the spacer fibers 105, at the surface of the spacer fibers 105, within the openings between the fibers 104, 105, and so forth. (Further examples of ways which agents may be disposed within slings are discussed elsewhere herein.)

Specific examples of collagenous-tissue-promoting agents may be selected, for example, from species that have been identified in tendon growth and/or healing processes, among other agents. In this regard, growth factors and other species (e.g., transforming growth factor beta (TGF-beta), epidermal growth factor (EGF), platelet-derived growth factor (PDGF), insulin-like growth factor (IGF), basic fibroblast growth factor (bFGF), vascular endothelial growth factor (VEGF), substance P, etc.) may be incorporated into the fibers in some embodiments. See, e.g., the following: X. T. Wang et al., "Tendon Healing In Vitro: bFGF Gene Transfer to Tenocytes by Adeno-Associated Viral Vectors Promotes Expression of Collagen Genes," *Hand Surg [Am]*. 2005 November; 30(6): 1255-61; P. Burssens et al., "Exogenously administered substance P and neutral endopeptidase inhibitors stimulate fibroblast proliferation, angiogenesis and collagen organization during Achilles tendon healing," *Foot Ankle Int*. 2005 October; 26(10): 832-9; S. Thomopoulos et al., "Effect of several growth factors on canine flexor tendon fibroblast proliferation and collagen synthesis in vitro," *J Hand Surg [Am]*. 2005 May; 30(3): 441-7 (a combination of PDGF-BB and bFGF led to an increase in fibroblast proliferation but no change in collagen production compared with each factor alone, cell proliferation and collagen production were unchanged with VEGF and BMP-2); and T. Tsubone et al., "Expression of growth factors in canine flexor tendon after laceration in vivo," *Ann Plast Surg*. 2004 October; 53(4): 393-7 (TGF-beta, EGF, PDGF-AA, PDGF-BB, IGF, bFGF and VEGF are all expressed at 10 days after tendon injury in and around the repair site). Synthetic growth factors are available from various sources. For example, FGF analogs are available from BioSurface Engineering Technologies, Inc. (BioSET), of College Park, Md., USA.

Figure 4:
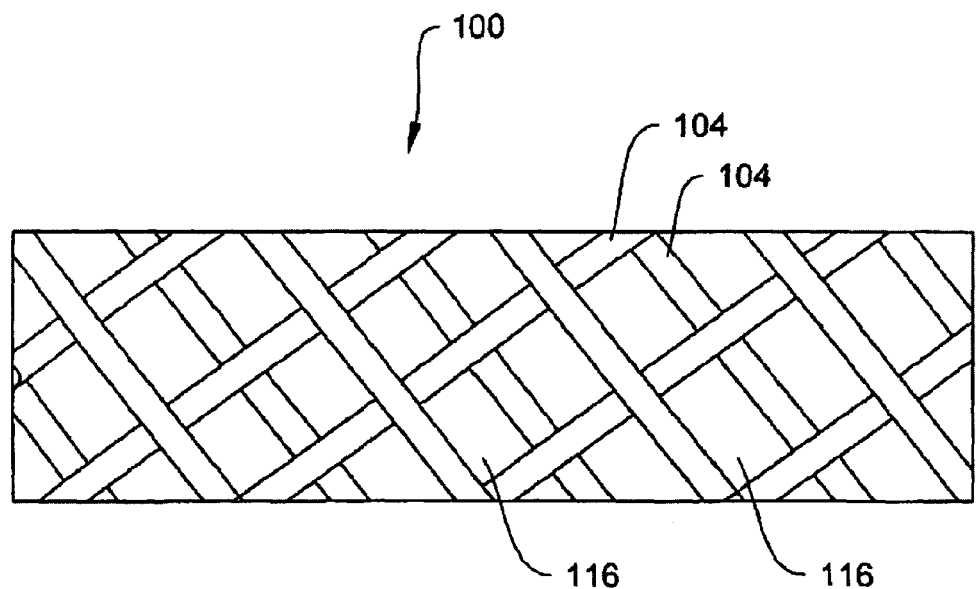
FIG. 4 is a view of a surgical sling according to another illustrative embodiment of the invention.
Figure 5:
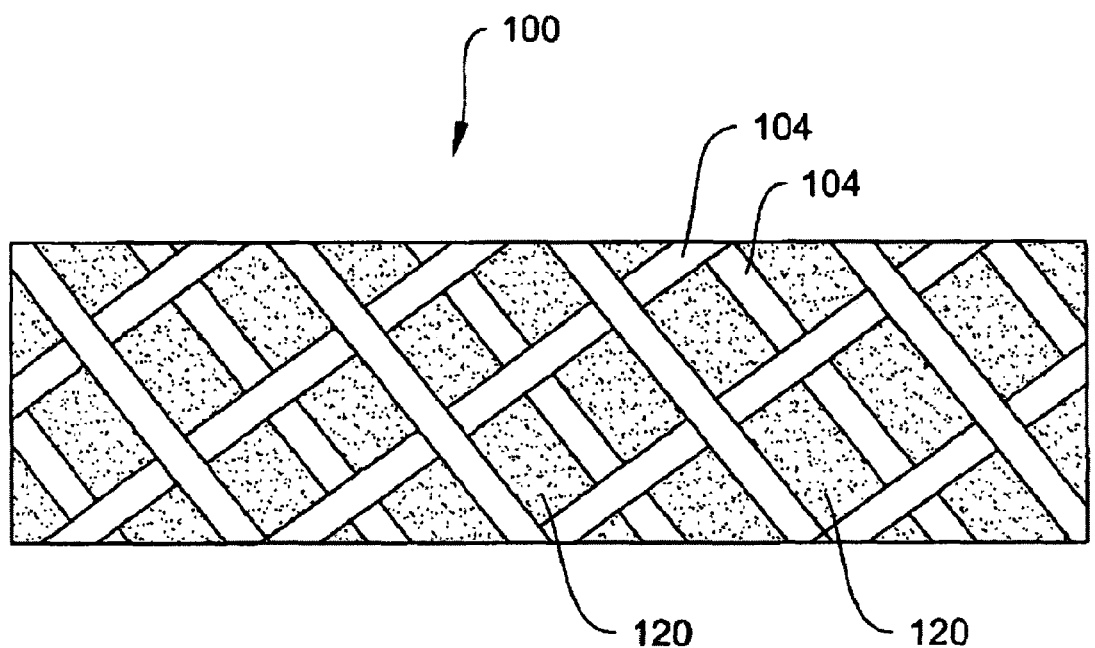
FIG. 5 is a view of the sling of FIG. 4 including a hydrogel coating according to an illustrative embodiment of the invention.

In another illustrative embodiment of the surgical sling 100, as depicted in FIG. 4, the fibers 104 of the surgical sling 100 define one or more openings 116 in the sling 100. The openings 116 may assume any shape or size relative to the sling 100. As illustrated in FIG. 5, a hydrogel coating 120, which contains the agent 108, and which, preferably, has a high enough viscosity to maintain the agent 108 in the openings 116, is applied to the sling 100 of FIG. 4 to fill the openings 116.

Referring again to FIG. 4, in an alternative illustrative embodiment, an absorbable foam material (not shown) is disposed into the openings 116. Alternatively, the foam material may be embedded into the sling 100 so as to be present in the openings 116. The foam material is then, for example, thermally bonded to the sling 100. The agent 108, for example, in solution, is subsequently applied to and absorbed by the foam material. The foam material may be manufactured from, for example, polyvinyl acetate (PVA), polyurethane, silicone, polyester, polyethylene, gelatin, hyaluronic acid, chitosan, regenerate cellulose, or other suitable materials.

Figure 6A:
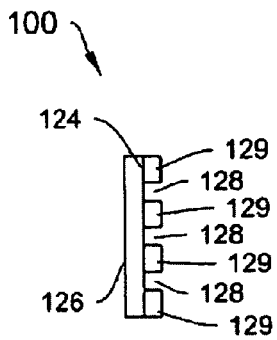
FIG. 6A is an exemplary end view of a sling according to another illustrative embodiment of the invention.
Figure 6B:
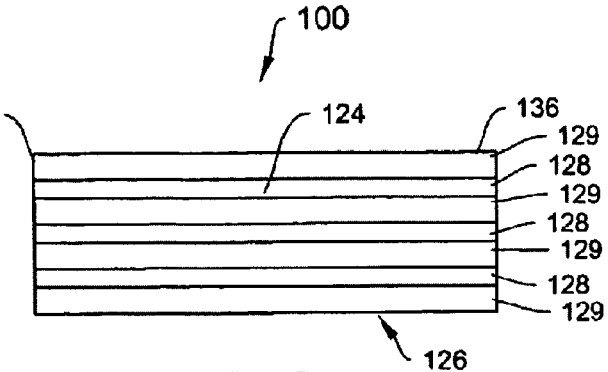
FIG. 6B is a top view of the illustrative surgical sling of FIG. 6A.
Figure 6C:
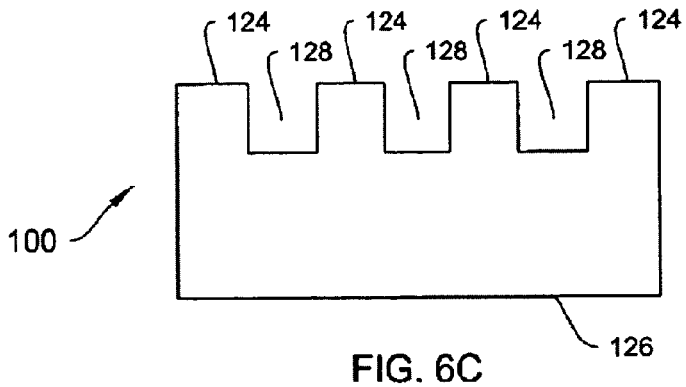
FIG. 6C is an end view showing an alternative to the illustrative embodiment of FIG. 6A.

According to another illustrative embodiment, the invention employs surface patterning on the surgical sling 100, alone or in combination with the agent 108, to promote well-organized collagenous tissue growth. Referring to FIGS. 6A-6C, in one illustrative embodiment, the first side 124 of the sling 100 includes one or more longitudinal channels 128. The channels 128 may be formed by longitudinally extending raised projections 129 on the first side 124, as illustrated in FIG. 6A. Alternatively, the channels 128 may be formed into the first side 124, as illustrated in FIG. 6C. As shown in FIG. 6B which is a view showing the first side 124, the channels 128 extend along the entire length of the surgical sing 100, from a first end 132 to a second end 136. However, this need not be the case. In alternative embodiments, the channels 128 extend an intermediate distance between the ends 132 and 136.

Figure 6D:
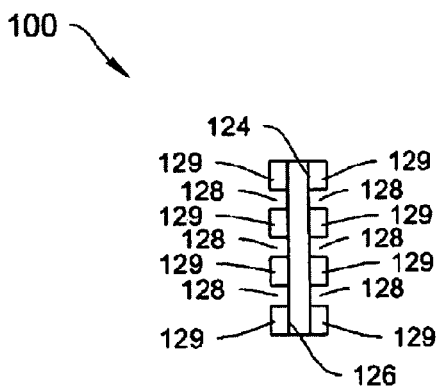
FIG. 6D is an end view of a sling employing channels along both its first and second sides according to an alternative illustrative embodiment of the invention.
Figure 6E:
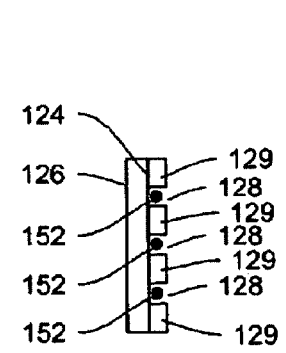
FIG. 6E is an end view of the illustrative sling of FIG. 6D, further depicting well-organized collagenous tissue growth.
Figure 9A:
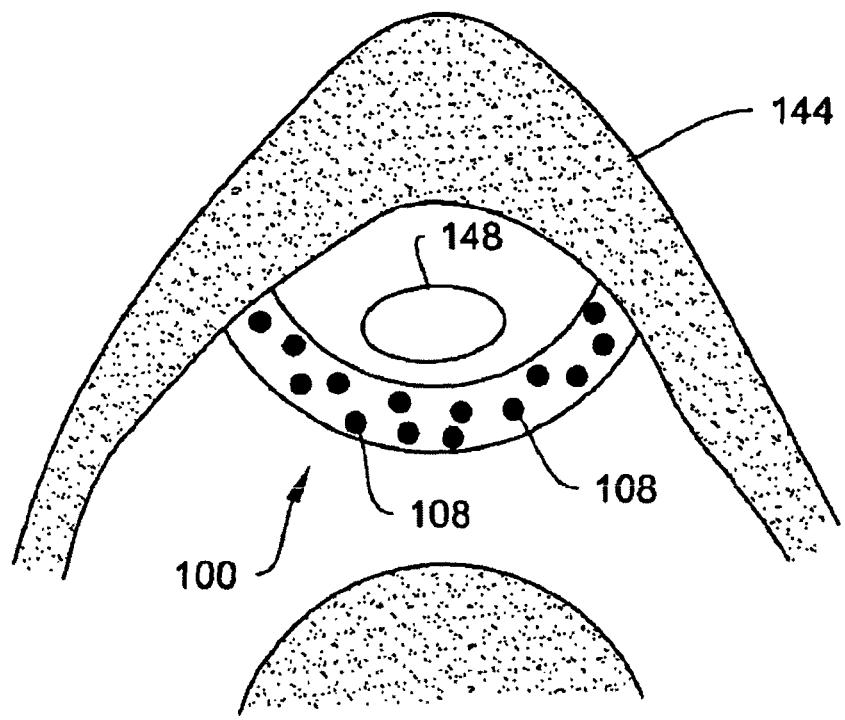
FIGS. 9A-9C depict one illustrative method for implanting a sling according to the invention in the body of a patient.

As shown in FIG. 6D, in other illustrative embodiments, the channels 128 may extend axially along both the first 124 and second 126 sides of the surgical sling 100. As discussed in further detail below with respect to FIGS. 9A-9C, and as indicated in FIG. 6E, as collagenous tissue growth occurs, the channels or surface pattern 128, engage the fibroblast cells and/or collagenous tissue 152 and improve cell/tissue attachment on to the sling and therefore guide its growth, such that the collagenous tissue 152, such as scar tissue, grows in the channels 128 as a well-organized, as opposed to a randomized, tissue 152.

Figure 7:
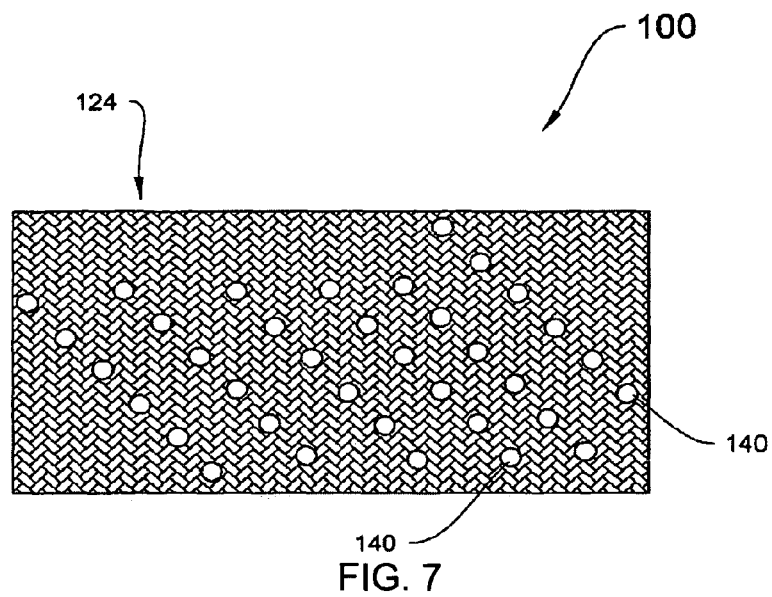
FIG. 7 is a view of a sling according to another alternative illustrative embodiment of the invention.

Referring now to FIG. 7, the surgical sling 100 may include one or more through holes/apertures 140. In the illustrative embodiment of FIG. 7, the through holes 140 are formed as perforations that pass from the first side 124 through to the second side 126 of the surgical sling 100. Following stimulation of the patient's surrounding (e.g., periurethral) tissues by the agent 108, through holes 140 engage the resulting collagenous tissue 152. The collagenous tissue 152 grows in such a manner as to pass in and out of the through holes 140 and incorporate the surgical sling 100. As such, the tissue 152 grows in a well-organized, as opposed to a randomized, manner surrounding the sling and/or sling fibers.

The sides 124 and/or 126 of the surgical sling 100 may, in other illustrative embodiments, include other patterns or designs to promote fibroblast proliferation, and the well-organized collagenous tissue growth. For example, the sides 124 and/or 126 may include texturing/roughening, such as, without limitation, one or more projections, depressions, rises, ridges, valleys, embossing, or combinations of any thereof. The texture may be formed by employing fibers 104 having various cross-sectional shapes, such as, circular, ovoid, square, rectangular, channeled (e.g., star or other cross-section resulting in a longitudinal groove down the length of the fiber), or other regular or irregular shapes. The surgical sling 100 may also includes portions having a varying thickness and/or width, which may be achieved, for example, by employing fibers 104 having varying diameters and/or by changing knit and/or weave density. Other patterns and designs may be formed on the sides 124 and 126 of the surgical sling 100 by any suitable approach.

Figure 9B:
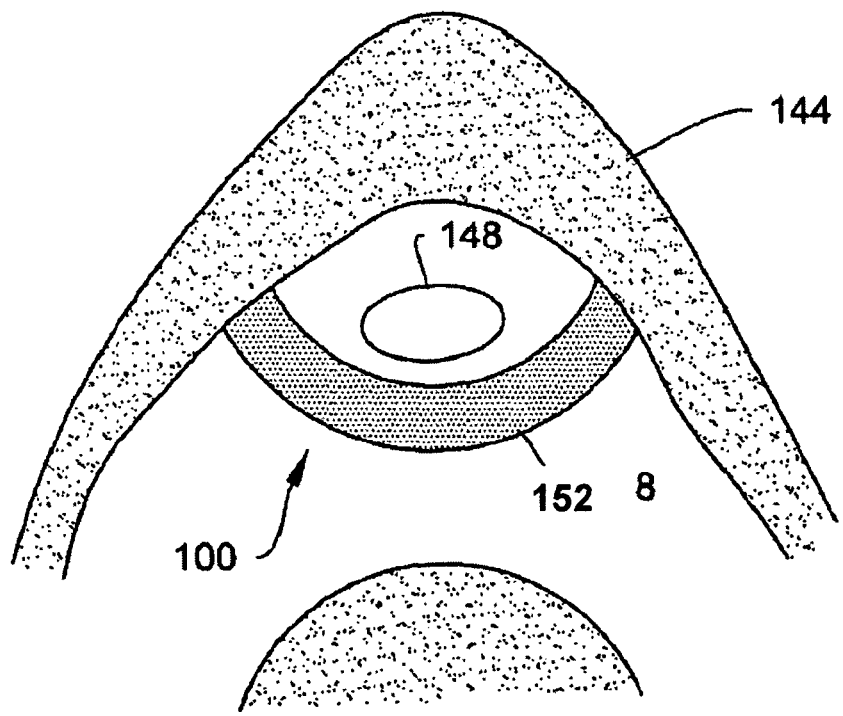
Figure 9C:
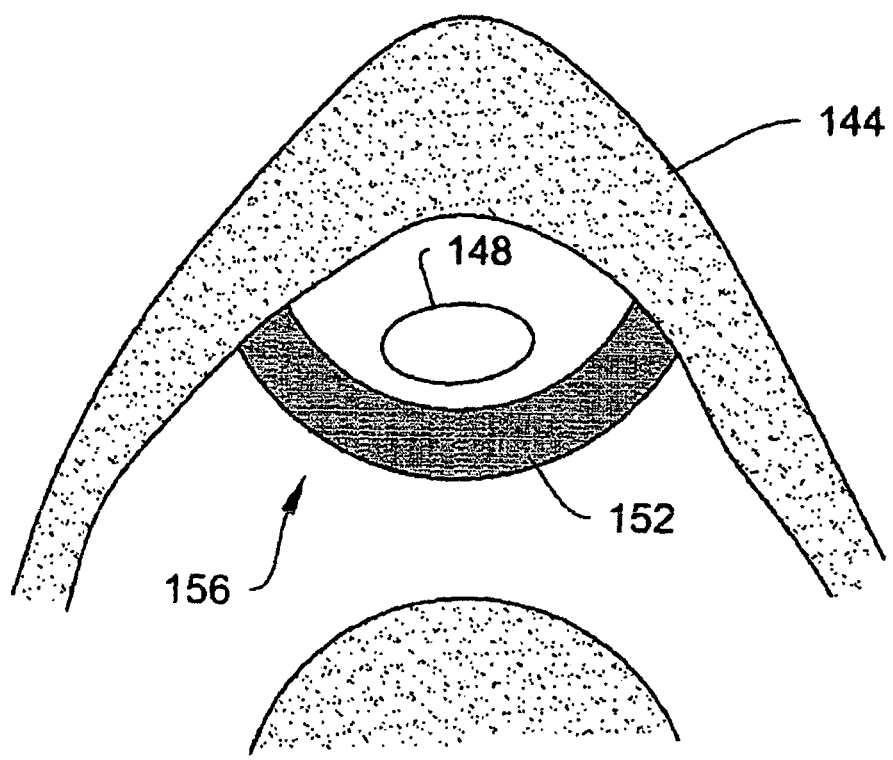

In other illustrative embodiments, the invention provides methods for treating urinary incontinence. Generally, referring to FIG. 9A, the surgical sling 100 is implanted in a patient's periurethral tissues 144 and positioned adjacent the patient's urethra 148. Initially, the surgical sling 100 provides physical support to the patient's urethra 148. The sling 100 releases the agent 108 into tissue near the implantation site to stimulate collagenous tissue growth. According to one feature, the structure of the surgical sling 100 encourages well-organized collagenous tissue growth. Referring now to FIG. 9B, after a pre-determined period of time, such as, for example, about two (2) to about eight (8) weeks, newly formed tissue 152 begins to support the patient's urethra 148. As illustrated in FIG. 9C, in one illustrative embodiment, the sling 100 is biodegradable, and after an additional pre-determined period of time, such as, for example, about three (3) to about six (6) months, the sling 100 is completely biodegraded. A natural tissue based sling 156, formed from the collagenous tissue 152, is left behind in the patient's periurethral tissues 144, adjacent the urethra 148. The natural tissue based sling 156 provides the requisite support to assist in maintaining continence. The natural tissue based sling 156 may be capable of adjusting itself to the anatomy of the patient's body changes without causing injury to the patient, such as increase in necessary length as the body gains additional weight.

Variations, modifications, and other implementations of what is described may be employed without departing from the spirit and the scope of the invention.

The invention claimed is:

1. A surgical implant comprising a surgical sling for implantation at an anatomical site in a body of a patient, the surgical sling including:
   a central portion;
   a first end portion including a first plurality of biostable fibers, the first end portion being disposed at a first end of the central portion; and
   a second end portion including a second plurality of biostable fibers, the second end portion being disposed at a second end of the central portion opposite the first end of the central portion, the central portion defining a longitudinal axis,
   the central portion including:
      a first plurality of fibers aligned in a first direction, the first direction being along the longitudinal axis; and
      a second plurality of fibers aligned in a second direction, the second direction being different than the first direction, the first plurality of fibers, upon implantation, promoting collagenous tissue growth.

2. The surgical implant of claim 1, wherein the surgical sling is a urethral sling.

3. The surgical implant of claim 1, wherein fibers of the first plurality of fibers of the central portion are biodegradable fibers that include a therapeutic agent that promotes collagenous tissue growth.

4. The surgical implant of claim 1, wherein a spacing between adjacent fibers of the first plurality of fibers of the central portion is less than a spacing between adjacent fibers of the second plurality of fibers of the central portion.

5. The surgical implant of claim 1, wherein fibers of the first plurality of fibers of the central portion include a biodegradable polymer.

6. The surgical implant of claim 1, wherein fibers of the first plurality of fibers of the central portion include a biodegradable polymer that is selected from polysachharides, poly(amino acids), polyesters, polyanhydrides, and combinations thereof.

7. The surgical implant of claim 1, wherein fibers of the first plurality of fibers of the central portion include a biodegradable polymer selected from hyaluronic acid, chitosan, collagen, fibronectin, poly(L-lactide), poly(D,L-lactide), poly(L-lactide-co-glycolide), poly(D,L-lactide-co-glycolide), and combinations thereof.

8. The surgical implant of claim 1, wherein fibers of the first plurality of fibers of the central portion include a polymer species that promotes cellular attachment and the second plurality of fibers of the central portion include a polymer species that inhibits cellular attachment.

9. The surgical implant of claim 8, wherein the polymer species that promotes cellular attachment is selected from ROD-peptide-containing-species, extracellular matrix components, and combinations thereof.

10. The surgical implant of claim 1, wherein fibers of the second plurality of fibers of the central portion include a collagenous-tissue-inhibiting agent.

11. The surgical implant of claim 1, wherein fibers of the first plurality of fibers of the central portion include a collagenous-tissue-promoting agent selected from cytokines, cells, sclerosing agents, and combinations thereof.

12. The surgical implant of claim 1, wherein fibers of the first plurality of fibers of the central portion include a collagenous-tissue-promoting agent selected from platelet-derived growth factor, fibroblast growth factor, substance P, and combinations thereof.

13. The surgical implant of claim 1, wherein fibers of the first plurality of fibers have diameters ranging from 5 μm to 50 μm.

14. The surgical implant of claim 1, wherein fibers of the first plurality of fibers of the central portion have a hydrophilic surface.

15. The surgical implant of claim 14, wherein fibers of the second plurality of fibers of the central portion have a hydrophobic surface.

16. The surgical implant of claim 14, wherein the second plurality of fibers of the central portion are biostable.

17. The surgical implant of claim 14, wherein a spacing between fibers of the first plurality of fibers of the central portion is based on at least one of a spacing between fibers of the second plurality of fibers of the central portion and a diameter of the fibers of the second plurality of fibers of the central portion.

18. The surgical implant of claim 14, wherein the second plurality of fibers of the central portion are interwoven with the first plurality of fibers of the central portion.

19. The surgical implant of claim 14, wherein fibers of the first plurality of fibers of the central portion have a longitudinally grooved surface and fibers of the second plurality of fibers of the central portion have a smooth surface.

20. The surgical implant of claim 19, wherein fibers of the first plurality of fibers of the central portion have a diameter or surface texture that promotes encapsulation by collagenous tissue growth and fibers of the second plurality of fibers of the central portion have a diameter or surface texture that inhibits encapsulation by collagenous tissue growth.

* * * * *